(12) United States Patent
Brånalt et al.

(10) Patent No.: US 8,119,673 B2
(45) Date of Patent: Feb. 21, 2012

(54) COMPOUNDS 148

(75) Inventors: Jonas Brånalt, Mölndal (SE); David Gustafsson, Mölndal (SE); Ingemar Nilsson, Mölndal (SE); Magnus Polla, Mölndal (SE)

(73) Assignee: AstraZeneca AB, Sodertalje (SE)

( * ) Notice: Subject to any disclaimer, the term of this patent is extended or adjusted under 35 U.S.C. 154(b) by 242 days.

(21) Appl. No.: 12/489,458

(22) Filed: Jun. 23, 2009

(65) Prior Publication Data

US 2009/0318517 A1 Dec. 24, 2009

Related U.S. Application Data

(60) Provisional application No. 61/102,381, filed on Oct. 3, 2008, provisional application No. 61/074,736, filed on Jun. 23, 2008.

(51) Int. Cl.
*A61K 31/41* (2006.01)
*C07D 257/04* (2006.01)

(52) U.S. Cl. ........................................ 514/381; 548/253

(58) Field of Classification Search .................. 548/253; 514/381
See application file for complete search history.

(56) References Cited

U.S. PATENT DOCUMENTS

| | | |
|---|---|---|
| 6,288,077 B1 | 9/2001 | De Nanteuil et al. |
| 6,515,011 B2 | 2/2003 | Selnick et al. |
| 6,528,503 B2 | 3/2003 | Williams et al. |
| 7,144,899 B2 | 12/2006 | Selnick et al. |
| 2004/0073025 A1 | 4/2004 | Selnick et al. |

FOREIGN PATENT DOCUMENTS

| | | |
|---|---|---|
| EP | 0641779 | 8/1994 |
| WO | 9911606 | 3/1999 |
| WO | 0044335 | 8/2000 |
| WO | 0187879 | 11/2001 |
| WO | 03018551 | 3/2003 |
| WO | 2004032834 | 4/2004 |
| WO | 2005054200 | 6/2005 |
| WO | 2008067909 | 6/2008 |
| WO | 2009004383 | 1/2009 |
| WO | 2009146802 | 12/2009 |

OTHER PUBLICATIONS

Lange et al., "Orally active thrombin inhibitors. Part 2: optimization of the P2-moiety," Bioorganic and Medicinal Chemistry Letters (2006) 16(10):2648-2653.

Deswal et al., "Quantitative structure activity relationship studies of aryl heterocycle-based thrombin inhibitors," European Journal of Medicinal Chemistry (2006) 41(11):1339-1346.

Staas et al., "Discovery of potent, selective 4-fluoroproline-based thrombin inhibitors with improved metabolic stability," Bioorganic & Medicinal Chemistry (2006) 14(20):6900-6916.

Young et al., "Discovery and evaluation of potent P1 aryl heterocycle-based thrombin inhibitors," Journal of Medicinal Chemistry (2004) 47:2995-3008.

*Primary Examiner* — Rebecca Anderson
(74) *Attorney, Agent, or Firm* — Pepper Hamilton LLP

(57) ABSTRACT

This invention relates to novel pharmaceutically useful compounds of formula (I), in particular compounds that are competitive inhibitors of trypsin-like serine proteases, especially thrombin, their use as medicaments, pharmaceutical compositions containing them and synthetic routes to their production.

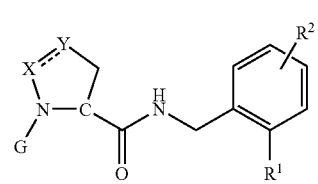

(I)

4 Claims, No Drawings

COMPOUNDS 148

CROSS-REFERENCE TO RELATED APPLICATIONS

This application claims priority under 35 U.S.C. §119(e) to U.S. Ser. No. 61/102,381 filed Oct. 3, 2008 and to U.S. Ser. No. 61/074,736 filed Jun. 23, 2008, each of which is incorporated herein by reference in its entirety.

FIELD OF THE INVENTION

This invention relates to novel pharmaceutically useful compounds, in particular compounds that are competitive inhibitors of trypsin-like serine proteases, especially thrombin, their use as medicaments, pharmaceutical compositions containing them and synthetic routes to their production.

BACKGROUND

Blood coagulation is the key process involved in both haemostasis (i.e. the prevention of blood loss from a damaged vessel) and thrombosis (i.e. the formation of a blood clot in a blood vessel, sometimes leading to vessel obstruction).

Coagulation is the result of a complex series of enzymatic reactions. One of the ultimate steps in this series of reactions is the conversion of the proenzyme prothrombin to the active enzyme thrombin.

Thrombin is known to play a central role in coagulation. It activates platelets, leading to platelet aggregation, converts fibrinogen into fibrin monomers, which polymerise spontaneously into fibrin polymers, and activates factor XIII, which in turn crosslinks the polymers to form insoluble fibrin. Furthermore, thrombin activates factor V, factor VIII and factor XI leading to a "positive feedback" generation of thrombin from prothrombin.

By inhibiting the aggregation of platelets and the formation and crosslinking of fibrin, effective inhibitors of thrombin would be expected to exhibit antithrombotic activity. In addition, antithrombotic activity would be expected to be enhanced by effective inhibition of the positive feedback mechanism. Indeed, the convincing antithrombotic effects of a thrombin inhibitor in man have been described by S. Schulman et al. in *N. Engl. J. Med.* 349, 1713-1721 (2003), L. Wallentin et al. in *Lancet* 362, 789-97 (2003) and H.-C. Diener et al. in *Cerebrovasc. Dis.* 21, 279-293 (2006).

The early development of low molecular weight inhibitors of thrombin has been described by Claesson in *Blood Coagul. Fibrinol.* 5, 411 (1994).

Blombäck et al. (in *J. Clin. Lab. Invest.* 24, suppl. 107, 59 (1969)) reported thrombin inhibitors based on the amino acid sequence situated around the cleavage site for the fibrinogen Aα chain. Of the amino acid sequences discussed, these authors suggested the tripeptide sequence Phe-Val-Arg (P9-P2-P1, hereinafter referred to as the P3-P2-P1 sequence) would be the most effective inhibitor.

Thrombin inhibitors based (at the P1-position of the molecule) upon the 2-heteroaromatic substituted 1-yl-benzylamide structural unit are disclosed in U.S. Pat. No. 7,144,899 and WO2004032834.

Thrombin inhibitors based (at the P2-position of the molecule) upon the 1-acetyl-pyrrolidine-2-carboxylic acid amide, 1-acetyl-piperidine-2-carboxylic acid amide or 1-acetyl-azepane-2-carboxylic acid amide structural units are disclosed in U.S. Pat. No. 7,144,899.

Thrombin inhibitors based (at the P2-position of the molecule) upon the 1-acetyl-pyrrolidine-2-carboxylic acid amide or 1-acetyl-dihydropyrrole-2-carboxylic acid amide structural units are disclosed in U.S. Pat. No. 6,515,011 and WO2004032834.

Thrombin inhibitors based (at the P2-position of the molecule) upon the 1-acetyl-azepane-2-carboxylic acid amide structural unit are disclosed in U.S. Pat. No. 6,528,503.

Thrombin inhibitors based (at the P2-position of the molecule) upon the aza-bicyclo[3.1.0]hexane-1-carboxylic acid amide structural unit are disclosed in U.S. Pat. No. 6,288,077.

Thrombin inhibitors based (at the P2-position of the molecule) upon the 1,3-thiazolidine-2-carboxylic acid amide, 1,3-thiazolidine-4-carboxylic acid amide, pyrazolidine-3-carboxylic acid amide and 4,5-dihydro-1H-pyrazole-5-carboxylic acid amide structural units are disclosed in U.S. Pat. No. 6,740,647 and also described by Lange et al. in *Bioorganic & Medicinal Chemistry Letters* 16, 2648-2653 (2006).

Quantitative structure activity relationship studies of aryl heterocycle-based thrombin inhibitors are described by Roy et al. in *European Journal of Medicinal Chemistry* 41, 1339-1346 (2006).

Thrombin inhibitors based (at the P2-position of the molecule) upon 4-fluoroprolines are described by Staas et al. in *Bioorganic & Medicinal Chemistry* 14, 6900-6916 (2006).

Thrombin inhibitors based (at the P2-position of the molecule) upon pyrazinones carrying various aryl-heterocycles at the P1-position of the molecule are described by Young et al. in *Journal of Medicinal Chemistry* 47, 2995-3008 (2004).

There remains a need for effective inhibitors of trypsin-like serine proteases, such as thrombin. There is also a need for compounds that have a favourable pharmacokinetic profile. Such compounds would be expected to be useful as anticoagulants and therefore in the therapeutic treatment of thrombosis and related disorders.

DISCLOSURE OF THE INVENTION

In one aspect of the present invention there is provided a compound of formula (I)

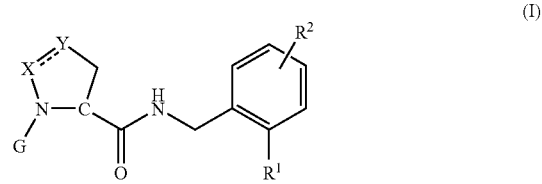

(I)

wherein

X is N, O or NH;

Y is $CH_2$ when X is O or NH, with X and Y connected via a single bond, or, alternatively, Y is CH when X is N, with X and Y connected via a double bond;

$R^1$ is a 5-membered heteroaryl ring containing 2, 3 or 4 heteroatoms, selected from N, O and S, wherein at least 2 heteroatoms are N, and 0 or 1 heteroatoms are O or S, wherein said 5-membered heteroaryl ring is substituted, at any carbon ring atom, by 0, 1 or 2 substituents independently selected from $C_{1-6}$ alkyl and a 6-membered heteroaryl ring containing 1 or 2 nitrogen atoms, wherein said 6-membered heteroaryl ring is substituted, at any carbon ring atom, by 0, 1, 2 or 3 substituents independently selected from $C_{1-6}$ alkyl;

$R^2$ is H, halogen, cyano, $C_{1-6}$ alkyl or $C_{1-6}$ alkoxy, wherein said $C_{1-6}$ alkyl or $C_{1-6}$ alkoxy is substituted by 0, 1, 2, 3, 4 or 5 halogen;

G represents

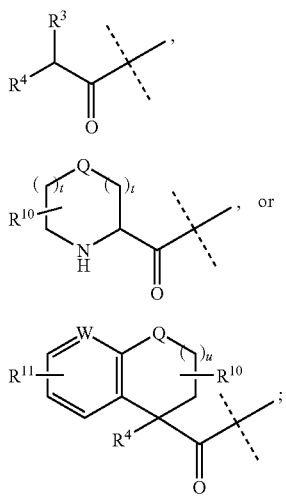

wherein
R³ is H, R⁵, $C_{1-6}$ alkyl, $C_{2-6}$ alkenyl, $C_{2-6}$ alkynyl or $C_{3-6}$ cycloalkyl, wherein each of said $C_{1-6}$ alkyl, $C_{2-6}$ alkenyl, $C_{2-6}$ alkynyl and $C_{3-6}$ cycloalkyl are independently substituted by 0, 1, 2, 3, 4 or 5 substituents selected from halogen and 0, 1 or 2 substituents selected from OH, oxo, cyano, $NH_2$, $NH(C_{1-4}$ alkyl), $N(C_{1-4}$ alkyl$)_2$, $C_{1-4}$ alkyl, $C_{3-6}$ cycloalkyl, $C_{4-7}$ cycloalkenyl, cycloheteroalkyl, R⁵ and R⁶;
R⁵ is phenyl,
a 5 or 6-membered heteroaromatic ring containing 1, 2 or 3 heteroatoms independently selected from O, S and N,
a 4-, 5- or 6-membered cycloheteroalkyl ring containing 1 or 2 heteroatoms independently selected from O, S and N or
a phenyl-fused 5- or 6-membered cycloheteroalkyl ring containing 1 or 2 heteroatoms independently selected from O, S and N, wherein said phenyl, said heteroaromatic ring, said cycloheteroalkyl ring and said phenyl-fused cycloheteroalkyl ring are substituted, at any carbon ring atom, by 0, 1, 2, 3, 4 or 5 substituents independently selected from COOH, OH, halogen, $CF_3$, $CHF_2$, $CH_2F$, cyano, $C_{1-6}$ alkyl, R⁶ and $SO_2R^7$;
R⁶ is $C_{1-6}$ alkoxy, wherein said $C_{1-6}$ alkoxy is substituted by 0, 1, 2, 3, 4 or 5 halogen;
R⁷ is $C_{1-6}$ alkyl;
R⁴ is OH, OC(O)R⁷, OC(O)R⁸ or NHR⁹;
R⁸ is phenyl, wherein said phenyl is substituted by 0, 1, 2, 3, 4 or 5 substituents independently selected from $C_{1-4}$ alkyl, $C_{1-4}$ alkoxy, cyano, F, $CF_3$, $CHF_2$ and $CH_2F$ or
$C_{1-4}$ alkyl, wherein said $C_{1-4}$ alkyl is substituted by 0, 1, 2 or 3 substituents independently selected from methyl and ethyl and 0 or 1 substituents selected from phenyl, wherein said phenyl is substituted by 0, 1, 2, 3, 4 or 5 substituents independently selected from $C_{1-4}$ alkyl, $C_{1-4}$ alkoxy, cyano F, $CF_3$, $CHF_2$, $CH_2F$ and OC(O)R⁷;
R⁹ is H, COOR⁷ or $SO_2R^7$ wherein said R⁷ is substituted by 0, 1, 2 or 3 substituents independently selected from OH, halogen, cyano, R⁶ and $C_{3-7}$ cycloalkyl;
Q is O, $CH_2$ or $S(O)_n$;
W is C or N;
n is independently 0, 1 or 2;
t is independently 0, 1 or 2;
u is independently 0 or 1;
R¹⁰ is 0, 1, 2, 3, 4 or 5 substituents selected from halogen, OH, oxo, cyano, $C_{1-4}$ alkyl, $C_{3-6}$ cycloalkyl, R⁵ and R⁶, wherein said $C_{1-4}$ alkyl is substituted by 0 or 1 substituent selected from R⁵, $NH_2$, $NH(C_{1-4}$ alkyl) or $N(C_{1-4}$ alkyl$)_2$; and
R¹¹ is 0, 1, 2, 3, 4 or 5 substituents selected from halogen, OH, cyano, $C_{1-4}$ alkyl, $C_{3-6}$ cycloalkyl, R⁵ and R⁶, wherein said $C_{1-4}$ alkyl is substituted by 0 or 1 substituent selected from R⁵, $NH_2$, $NH(C_{1-4}$ alkyl) or $N(C_{1-4}$ alkyl$)_2$;
or a pharmaceutically acceptable salt or an enantiomer or a pharmaceutically acceptable salt of said enantiomer.

The compounds of formula (I) have chiral centres and some have geometric isomeric centres (E- and Z-isomers), and it is understood that the invention encompasses all such optical, diastereoisomeric and geometric isomers.

In one aspect of the invention there is provided the use of a compound of formula (I) in therapy.

In a further aspect of the invention there is provided the use of a compound of formula (I) in anticoagulant therapy.

In still a further aspect of the invention there is provided the use of a compound of formula (I) in the treatment of a condition where inhibition of thrombin is beneficial.

In still a further aspect of the invention there is provided the use of a compound of formula (I) in the treatment and prevention of thromboembolic disorders.

In still a further aspect of the invention there is provided a method of treatment of a condition where inhibition of thrombin is beneficial, which method comprises administration of a therapeutically effective amount of a compound of formula (I) to a person suffering from, or susceptible to, such a condition.

In still a further aspect of the invention there is provided a method of treatment and prevention of thromboembolic disorders, which method comprises administration of a therapeutically effective amount of a compound of formula (I) to a person suffering from, or susceptible to, thrombophilia conditions.

In a further aspect of the invention there is provided pharmaceutical formulations comprising a therapeutically effective amount of a compound of formula (I), in admixture with at least one pharmaceutically acceptable diluent, excipients and/or inert carrier.

In yet a further aspect of the invention there is provided a pharmaceutical formulation comprising a compound of formula (I) for use in the treatment of those conditions where inhibition of thrombin is beneficial, such as thrombo-embolism and/or conditions where anticoagulant therapy is indicated.

In another aspect of the invention there is provided a process for the preparation of compounds of formula (I), and the intermediates used in the preparation thereof.

These and other aspects of the present invention are described in greater detail herein below.

DETAILED DESCRIPTION OF THE INVENTION

The object of the present invention is to provide compounds that are competitive inhibitors of trypsin-like serine proteases, especially thrombin, their use as medicaments, pharmaceutical compositions containing them and synthetic routes to their production.

Listed below are definitions of various terms used in the specification and claims to describe the present invention.

For the avoidance of doubt it is to be understood that where in this specification a group is qualified by "hereinbefore defined", "defined hereinbefore" or "defined above" the said group encompasses the first occurring and broadest definition as well as each and all of the other definitions for that group.

For the avoidance of doubt it is to be understood that in this specification "$C_{1-6}$" means a carbon group having 1, 2, 3, 4, 5 or 6 carbon atoms and "$C_{1-4}$" means a carbon group having 1, 2, 3 or 4 carbon atoms.

In this specification, unless stated otherwise, the term "alkyl" includes both straight and branched chain alkyl groups and may be, but are not limited to, methyl, ethyl, n-propyl, i-propyl, n-butyl, i-butyl, s-butyl, t-butyl, n-pentyl, i-pentyl, t-pentyl, neo-pentyl, n-hexyl, i-hexyl or t-hexyl.

In this specification, unless stated otherwise, the term "cycloalkyl" refers to a saturated cyclic hydrocarbon ring system. The term "$C_{3-6}$ cycloalkyl" may be cyclopropyl, cyclobutyl, cyclopentyl or cyclohexyl.

In this specification, unless stated otherwise, the term "alkenyl" includes both straight and branched chain alkenyl groups. The term $C_{2-6}$ alkenyl includes alkenyl groups having 2 to 6 carbon atoms and one or two double bonds, and may be, but is not limited to, vinyl, allyl, propenyl, butenyl, crotyl, pentenyl, or hexenyl, and a butenyl group may for example be buten-2-yl, buten-3-yl or buten-4-yl.

In this specification, unless stated otherwise, the term "alkynyl" includes both straight and branched chain alkynyl groups. The term $C_{2-6}$ alkynyl includes alkynyl groups having 2 to 6 carbon atoms and one or two triple bonds, and may be, but is not limited to, etynyl, propargyl, pentynyl or hexynyl and a butynyl group may for example be butyn-3-yl or butyn-4-yl.

In this specification, unless stated otherwise, the term "cycloalkenyl" refers to a non-aromatic cyclic hydrocarbon ring system containing one or two double bonds. The term "$C_{4-7}$ cycloalkenyl" may be, but is not limited to, cyclobutenyl, cyclopentenyl, cyclohexenyl or cycloheptenyl and a cyclopentenyl group may for example be cyclopenten-3-yl or cyclopenten-4-yl.

In this specification, unless stated otherwise, the term "alkoxy" includes both straight or branched alkoxy groups. $C_{1-6}$ alkoxy may be, but is not limited to, methoxy, ethoxy, n-propoxy, i-propoxy, n-butoxy, i-butoxy, s-butoxy, t-butoxy, n-pentoxy, i-pentoxy, t-pentoxy, neo-pentoxy, n-hexyloxy, i-hexyloxy or t-hexyloxy.

In this specification, unless stated otherwise, the term "5-membered heteroaryl ring containing 2, 3 or 4 heteroatoms, selected from N, O and S, wherein at least 2 heteroatoms are N, and 0 or 1 heteroatoms are O or S" includes aromatic heterocyclic rings. Examples of such rings are imidazole, tetrazole, triazole, thiadiazole or oxadiazole.

In this specification, unless stated otherwise, the term "6-membered heteroaryl ring containing 1 or 2 nitrogen atoms" includes pyridine, pyridazine, pyrimidine or pyrazine.

In this specification, unless stated otherwise, the term "4-, 5- or 6-membered cycloheteroalkyl ring having 1 or 2 heteroatoms selected from O, S and N" includes oxetane, azetidine, oxazetidine, pyrrolidine, imidazoline, tetrahydrofuran, oxazolidine, piperidine, piperazine, hexahydropyridazine, hexahydropyrimidine, morpholine, oxazinane, thietane, thietane 1-oxide, thietane 1,1-dioxide, tetrahydra-thiophene, tetrahydra-thiophene 1-oxide, tetrahydra-thiophene 1,1-dioxide, tetrahydra-thiopyran, tetrahydra-thiopyran 1-oxide or tetrahydra-thiopyran 1,1-dioxide.

In this specification, unless stated otherwise, the term "5 or 6-membered heteroaromatic ring containing 1, 2 or 3 heteroatoms independently selected from O, S and N" includes furan, thiophene, pyrrole, oxazole, isoxazole, thiazole, isothiazole, imidazole, triazole, thiadiazole, oxadiazole, pyridine, pyridazine, pyrimidine, pyrazine or triazine.

In this specification, unless stated otherwise, the term "phenyl-fused 5- or 6-membered cycloheteroalkyl ring containing 1 or 2 heteroatoms independently selected from O, S and N" includes indoline, dihydroisoindole, dihydrobenzofuran, dihydroisobenzofuran, dihydrobenzothiophene, dihydrobenzoimidazole, dihydroindazole, dihydrobenzooxazole, dihydrobenzothiazole, tetrahydroquinoline, tetrahydroisoquinoline, tetrahydroquinoxaline, tetrahydraquinazoline, tetrahydrophtalazine, chroman, isochroman, thiochroman, isothiochroman, dihydrobenzooxazine or dihydrobenzothiazine.

In this specification, unless stated otherwise, the term "halogen" may be fluoro, chloro, bromo or iodo.

In this specification,

represents motifs of the following structures

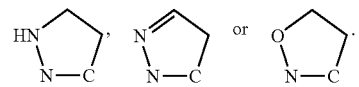

In one embodiment of the invention $R^1$ is a 5-membered heteroaryl ring containing 2, 3 or 4 heteroatoms, selected from N, O and S, wherein at least 2 heteroatoms are N, and 0 or 1 heteroatoms are O or S, wherein said 5-membered heteroaryl ring is substituted, at any carbon ring atom, by 0, 1 or 2 substituents independently selected from $C_{1-6}$ alkyl and a 6-membered heteroaryl ring containing 1 or 2 nitrogen atoms, wherein said 6-membered heteroaryl ring is substituted, at any carbon ring atom, by 0, 1, 2 or 3 substituents independently selected from $C_{1-6}$ alkyl.

In a further embodiment of the invention $R^1$ is a 5-membered heteroaryl ring containing 2, 3 or 4 heteroatoms, selected from N, O and S, wherein at least 2 heteroatoms are N, and 0 or 1 heteroatom is O or S.

In a further embodiment of the invention $R^1$ is tetrazole.

In one embodiment of the invention $R^2$ is H, halogen, cyano, $C_{1-6}$ alkyl or $C_{1-6}$ alkoxy, wherein said $C_{1-6}$ alkyl or $C_{1-6}$ alkoxy is substituted by 0, 1, 2, 3, 4 or 5 halogen.

In a further embodiment of the invention $R^2$ is H or halogen.

In still another embodiment of the invention $R^2$ is H, Cl or F.

In one embodiment of the invention the stereochemical configuration around the carbon in the pyrazolidine, dihydropyrazole or isoxazolidine, i.e. the ring containing X and Y, which is covalently bound to the carbonyl is (S).

In one embodiment of the invention G is

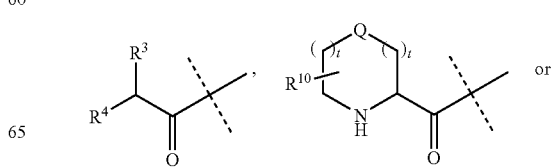

-continued

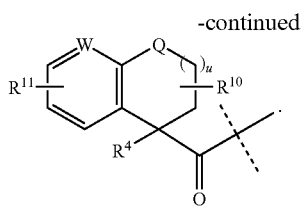

In a further embodiment of the invention G is

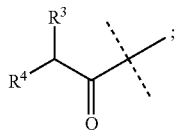

$R^3$ is H, $R^5$, $C_{1-6}$ alkyl, $C_{2-6}$ alkenyl, $C_{2-6}$ alkynyl or $C_{3-6}$ cycloalkyl, wherein each of said $C_{1-6}$ alkyl, $C_{2-6}$ alkenyl, $C_{2-6}$ alkynyl, and $C_{3-6}$ cycloalkyl are independently substituted by 0, 1, 2, 3, 4 or 5 substituents selected from halogen and 0, 1 or 2 substituents selected from OH, oxo, cyano, $NH_2$, $NH(C_{1-4}$ alkyl), $N(C_{1-4}$ alkyl$)_2$, $C_{1-4}$ alkyl, $C_{3-6}$ cycloalkyl, $C_{4-7}$ cycloalkenyl, cycloheteroalkyl, $R^5$ and $R^6$, wherein $R^5$ is phenyl, a 5 or 6-membered heteroaromatic ring containing 1, 2 or 3 heteroatoms independently selected from O, S and N, a 4-, 5- or 6-membered cycloheteroalkyl ring containing 1 or 2 heteroatoms independently selected from O, S and N or a phenyl-fused 5- or 6-membered cycloheteroalkyl ring containing 1 or 2 heteroatoms independently selected from O, S and N, wherein said phenyl, said heteroaromatic ring, said cycloheteroalkyl ring and said phenyl-fused cycloheteroalkyl ring are substituted, at any carbon ring atom, by 0, 1, 2, 3, 4 or 5 substituents independently selected from COOH, OH, halogen, $CF_3$, $CHF_2$, $CH_2F$, cyano, $C_{1-6}$ alkyl, $R^6$ and $SO_2R^7$;

$R^6$ is $C_{1-6}$ alkoxy, wherein said $C_{1-6}$ alkoxy is substituted by 0, 1, 2, 3, 4 or 5 halogen; and $R^7$ is $C_{1-6}$ alkyl;

$R^4$ is OH, $OC(O)R^7$, $OC(O)R^8$ or $NHR^9$;

$R^8$ is phenyl, wherein said phenyl is substituted by 0, 1, 2, 3, 4 or 5 substituents independently selected from $C_{1-4}$ alkyl, $C_{1-4}$ alkoxy, cyano, F, $CF_3$, $CHF_2$ and $CH_2F$ or $C_{1-4}$ alkyl, wherein said $C_{1-4}$ alkyl is substituted by 0, 1, 2 or 3 substituents independently selected from methyl and ethyl and 0 or 1 substituents selected from phenyl, wherein said phenyl is substituted by 0, 1, 2, 3, 4 or 5 substituents independently selected from $C_{1-4}$ alkyl, $C_{1-4}$ alkoxy, cyano, F, $CF_3$, $CHF_2$, $CH_2F$ and $OCOR^7$;

$R^9$ is H, $COOR^7$ or $SO_2R^7$ wherein said $R^7$ is substituted by 0, 1, 2 or 3 substituents independently selected from OH, halogen, cyano, $R^6$ and $C_{3-7}$ cycloalkyl;

wherein $R^6$ is $C_{1-6}$ alkoxy, wherein said $C_{1-6}$ alkoxy is substituted by 0, 1, 2, 3, 4 or 5 halogen; and $R^7$ is $C_{1-6}$ alkyl.

In a further embodiment of the invention G is

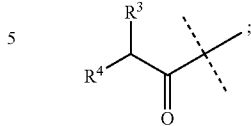

$R^3$ is $C_{1-6}$ alkyl, $C_{3-6}$ cycloalkyl, a 5 or 6-membered heteroaromatic ring containing 1, 2 or 3 heteroatoms independently selected from O, S and N,
a 4-, 5- or 6-membered cycloheteroalkyl ring containing 1 or 2 heteroatoms independently selected from O, S and N, or
$R^{12}$, wherein said $C_{1-6}$ alkyl, said $C_{3-6}$ cycloalkyl, said heteroaromatic ring and said cycloheteroalkyl ring are substituted by 0 or 1 substituents selected from $NH_2$, $NH(C_{1-4}$ alkyl), $N(C_{1-4}$ alkyl$)_2$, $C_3$ cycloalkyl, $R^6$ or $R^{12}$,
wherein $R^6$ is $C_{1-6}$ alkoxy, wherein said $C_{1-6}$ alkoxy is substituted by 0, 1, 2, 3, 4 or 5 halogen;
$R^{12}$ is phenyl, wherein said phenyl is substituted by 0, 1 or 2 substituents selected from halogen and $R^6$; and $R^4$ is OH, $OC(O)R^7$, $OC(O)R^8$ or $NH_2$,
wherein $R^7$ is $C_{1-6}$ alkyl;
$R^8$ is phenyl, wherein said phenyl is substituted by 0, 1, 2, 3, 4 or 5 substituents independently selected from $C_{1-4}$ alkyl, $C_{1-4}$ alkoxy, cyano, F, $CF_3$, $CHF_2$ and $CH_2F$ or $C_{1-4}$ alkyl, wherein said $C_{1-4}$ alkyl is substituted by 0, 1, 2 or 3 substituents independently selected from methyl and ethyl and 0 or 1 substituents selected from phenyl, wherein said phenyl is substituted by 0, 1, 2, 3, 4 or 5 substituents independently selected from $C_{1-4}$ alkyl, $C_{1-4}$ alkoxy, cyano, F, $CF_3$, $CHF_2$, $CH_2F$ and $OCOR^7$.

In a still further embodiment of the invention G is

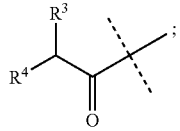

$R^3$ is $C_{3-6}$ cycloalkyl, $R^{12}$ or $C_{1-6}$ alkyl, wherein said $C_{1-6}$ alkyl is substituted by 0 or 1 substituents selected from $C_3$ cycloalkyl, $N(C_{1-4}$ alkyl$)_2$, $R^6$ or $R^{12}$,
wherein $R^6$ is $C_{1-6}$ alkoxy, wherein said $C_{1-6}$ alkoxy is substituted by 0, 1, 2, 3, 4 or 5 halogen; and
$R^{12}$ is phenyl, wherein said phenyl is substituted by 0, 1 or 2 substituents selected from halogen; and $R^4$ is OH or $OC(O)R^7$.

In one embodiment of the invention the stereochemical configuration around the carbon substituted by $R^3$ and $R^4$ in G is (R).

In a further embodiment G is

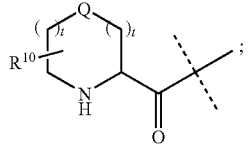

$R^{10}$ is 0, 1, 2, 3, 4 or 5 substituents selected from halogen, OH, oxo, cyano, $C_{1-4}$ alkyl, $C_{3-6}$ cycloalkyl, $R^5$ and $R^6$, wherein said $C_{1-4}$ alkyl is substituted by 0 or 1 substituent selected from $R^5$, $NH_2$, $NH(C_{1-4}$ alkyl) or $N(C_{1-4}$ alkyl$)_2$;

$R^5$ is phenyl, which is substituted, by 0, 1, 2, 3, 4 or 5 substituents independently selected from COOH, OH, halogen, $CF_3$, cyano, $C_{1-6}$ alkyl, $R^6$ and $SO_2R^7$,
 wherein $R^6$ is $C_{1-6}$ alkoxy, wherein said $C_{1-6}$ alkoxy is substituted by 0, 1, 2, 3, 4 or 5 halogen; and
 $R^7$ is $C_{1-6}$ alkyl;
Q is O, $CH_2$ or $S(O)_n$;
n is independently 0, 1 or 2; and
each t is independently 0, 1 or 2.

In a still further embodiment of the invention G is

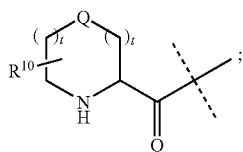

Q is O or $CH_2$;
each t is independently 0 or 1;
$R^{10}$ is 0, 1 or 2 substituents selected from oxo, $C_{1-4}$ alkyl, $R^5$ and $R^6$; and
$R^5$ is phenyl, which is substituted by 0, 1, 2, 3, 4 or 5 substituents independently selected from COOH, OH, halogen, $CF_3$, cyano, $C_{1-6}$ alkyl, $R^6$ and $SO_2R^7$;
 wherein $R^6$ is $C_{1-6}$ alkoxy, wherein said $C_{1-6}$ alkoxy is substituted by 0, 1, 2, 3, 4 or 5 halogen; and
 $R^7$ is $C_{1-6}$ alkyl;

In a still further embodiment of the invention G is

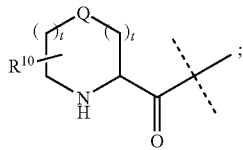

Q is O or $CH_2$; and
each t is independently 0 or 1; and
$R^{10}$ is 0, 1 or 2 substituents selected from oxo and $C_{1-4}$ alkyl.

In a further embodiment of the invention G is

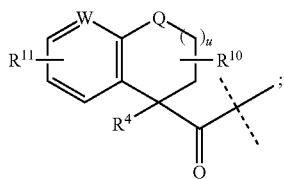

$R^4$ is OH, $OC(O)R^7$, $OC(O)R^8$ or $NHR^9$;
 wherein $R^7$ is $C_{1-6}$ alkyl;
 $R^8$ is phenyl, wherein said phenyl is substituted by 0, 1, 2, 3, 4 or 5 substituents independently selected from $C_{1-4}$ alkyl, $C_{1-4}$ alkoxy, cyano, F, $CF_3$, $CHF_2$ and $CH_2F$ or
 $C_{1-4}$ alkyl, wherein said $C_{1-4}$ alkyl is substituted by 0, 1, 2 or 3 substituents independently selected from methyl and ethyl and 0 or 1 substituents selected from phenyl, wherein said phenyl is substituted by 0, 1, 2, 3, 4 or 5 substituents independently selected from $C_{1-4}$ alkyl, $C_{1-4}$ alkoxy, cyano, F, $CF_3$, $CHF_2$, $CH_2F$ and $CO_2R^7$; and
 $R^9$ is H, $COOR^7$ or $SO_2R^7$ wherein said $R^7$ is substituted by 0, 1, 2 or 3 substituents independently selected from OH, halogen, cyano, $R^6$ and $C_{3-7}$ cycloalkyl;

Q is O, $CH_2$ or $S(O)_n$;
W is C or N;
n is independently 0, 1 or 2;
u is independently 0 or 1; and
$R^{10}$ is 0, 1, 2, 3, 4 or 5 substituents selected from halogen, OH, oxo, cyano, $C_{1-4}$ alkyl, $C_{3-6}$ cycloalkyl, $R^5$ and $R^6$, wherein said $C_{1-4}$ alkyl is substituted by 0 or 1 substituent selected from $R^5$, $NH_2$, $NH(C_{1-4}$ alkyl) or $N(C_{1-4}$ alkyl)$_2$;
$R^{11}$ is 0, 1, 2, 3, 4 or 5 substituents selected from halogen, OH, cyano, $C_{1-4}$ alkyl, $C_{3-6}$ cycloalkyl, $R^5$ and $R^6$, wherein said $C_{1-4}$ alkyl is substituted by 0 or 1 substituents selected from $R^5$, $NH_2$, $NH(C_{1-4}$ alkyl) or $N(C_{1-4}$ alkyl)$_2$;
 $R^5$ is phenyl, which is substituted, by 0, 1, 2, 3, 4 or 5 substituents independently selected from COOH, OH, halogen, $CF_3$, cyano, $C_{1-6}$ alkyl, $R^6$ and $SO_2R^7$,
 wherein $R^6$ is $C_{1-6}$ alkoxy, wherein said $C_{1-6}$ alkoxy is substituted by 0, 1, 2, 3, 4 or 5 halogen; and
 $R^7$ is $C_{1-6}$ alkyl.

In a still further embodiment of the invention G is

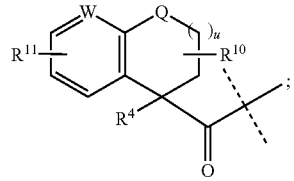

$R^4$ is OH, $OC(O)R^7$, $OC(O)R^8$ or $NH_2$,
 wherein $R^7$ is $C_{1-6}$ alkyl;
 $R^8$ is phenyl, wherein said phenyl is substituted by 0, 1, 2, 3, 4 or 5 substituents independently selected from $C_{1-4}$ alkyl, $C_{1-4}$ alkoxy, cyano, F, $CF_3$, $CHF_2$ and $CH_2F$ or
 $C_{1-4}$ alkyl, wherein said $C_{1-4}$ alkyl is substituted by 0, 1, 2 or 3 substituents independently selected from methyl and ethyl and 0 or 1 substituents selected from phenyl, wherein said phenyl is substituted by 0, 1, 2, 3, 4 or 5 substituents independently selected from $C_{1-4}$ alkyl, $C_{1-4}$ alkoxy, cyano, F, $CF_3$, $CHF_2$, $CH_2F$ and $CO_2R^7$;
Q is or $CH_2$;
u is independently 0 or 1; and
$R^{10}$ is 0, 1 or 2 substituents selected from $C_{1-4}$ alkyl, halogen and $R^6$;
$R^{11}$ is 0, 1 or 2 substituents selected from $C_{1-4}$ alkyl, halogen and $R^6$,
 wherein $R^6$ is $C_{1-6}$ alkoxy, wherein said $C_{1-6}$ alkoxy is substituted by 0, 1, 2, 3, 4 or 5 halogen.

In a still further embodiment of the invention G is

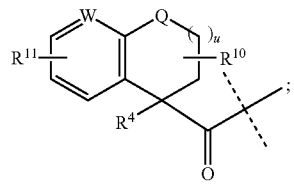

$R^4$ is OH or $OC(O)R^7$;
$R^{10}$ is 0, 1 or 2 substituents selected from $C_{1-4}$ alkyl, F, Cl, $OCH_3$, $OCF_3$, $OCHF_2$ and $OCH_2F$;
$R^{11}$ is 0, 1 or 2 substituents selected from $C_{1-4}$ alkyl, F, Cl, $OCH_3$, $OCF_3$, $OCHF_2$ and $OCH_2F$;
Q is O or $CH_2$; and
u is independently 0 or 1.

In one embodiment of the invention the compound of formula (I) is selected from:

(5S)—N-[5-Chloro-2-(1H-tetrazol-1-yl)benzyl]-1-[(2R)-2-(4-fluorophenyl)-2-hydroxyacetyl]-4,5-dihydro-1H-pyrazole-5-carboxamide, (5S)—N-[5-Chloro-2-(1H-tetrazol-1-yl)benzyl]-1-[(2,3-difluorophenyl)(hydroxy)acetyl]-4,5-dihydro-1H-pyrazole-5-carboxamide, (5S)-1-[(2R)-3-tert-Butoxy-2-hydroxypropanoyl]-N-[5-chloro-2-(1H-tetrazol-1-yl)benzyl]-4,5-dihydro-1H-pyrazole-5-carboxamide, (5S)—N-[5-Chloro-2-(1H-tetrazol-1-yl)benzyl]-1-[(3,5-difluorophenyl)(hydroxy)acetyl]-4,5-dihydro-1H-pyrazole-5-carboxamide, (5S)—N-[5-Chloro-2-(1H-tetrazol-1-yl)benzyl]-1-[(2R)-2-cyclopentyl-2-hydroxyacetyl]-4,5-dihydro-1H-pyrazole-5-carboxamide, (5S)—N-[5-Chloro-2-(1H-tetrazol-1-yl)benzyl]-1-[(2,4-difluorophenyl)(hydroxy)acetyl]-4,5-dihydro-1H-pyrazole-5-carboxamide, (5S)—N-[5-Chloro-2-(1H-tetrazol-1-yl)benzyl]-1-[(2R)-2-hydroxy-2-(3-methylphenyl)acetyl]-4,5-dihydro-1H-pyrazole-5-carboxamide, (5S)—N-[5-Chloro-2-(1H-tetrazol-1-yl)benzyl]-1-[(2R)-2-hydroxy-5-methylhexanoyl]-4,5-dihydro-1H-pyrazole-5-carboxamide, (5S)—N-[5-Chloro-2-(1H-tetrazol-1-yl)benzyl]-1-[(2-fluorophenyl)(hydroxy)acetyl]-4,5-dihydro-1H-pyrazole-5-carboxamide, (5S)—N-[5-Chloro-2-(1H-tetrazol-1-yl)benzyl]-1-[(2R)-2-hydroxyhexanoyl]-4,5-dihydro-1H-pyrazole-5-carboxamide, (5S)—N-[5-Chloro-2-(1H-tetrazol-1-yl)benzyl]-1-[(2R)-2-hydroxy-3-(1-methylcyclopropyl)propanoyl]-4,5-dihydro-1H-pyrazole-5-carboxamide, (5S)—N-[5-Chloro-2-(1H-tetrazol-1-yl)benzyl]-1-[(4-hydroxy-3,4-dihydro-2H-chromen-4-yl)carbonyl]-4,5-dihydro-1H-pyrazole-5-carboxamide, (5S)—N-[5-Chloro-2-(1H-tetrazol-1-yl)benzyl]-1-[(2R)-2-hydroxy-2-phenylacetyl]-4,5-dihydro-1H-pyrazole-5-carboxamide, (5S)—N-[5-Chloro-2-(1H-tetrazol-1-yl)benzyl]-1-[(2R)-2-hydroxy-4,4-dimethylpentanoyl]-4,5-dihydro-1H-pyrazole-5-carboxamide, (5S)—N-[5-Chloro-2-(1H-tetrazol-1-yl)benzyl]-1-[(2R)-2-cyclohexyl-2-hydroxyacetyl]-4,5-dihydro-1H-pyrazole-5-carboxamide, (5S)—N-[5-Chloro-2-(1H-tetrazol-1-yl)benzyl]-1-[(2R)-2-hydroxy-3-methoxy-3-methylbutanoyl]-4,5-dihydro-1H-pyrazole-5-carboxamide, (5S)—N-[5-Chloro-2-(1H-tetrazol-1-yl)benzyl]-1-[(2R)-2-hydroxy-3-phenylpropanoyl]-4,5-dihydro-1H-pyrazole-5-carboxamide, (5S)—N-[5-Chloro-2-(1H-tetrazol-1-yl)benzyl]-1-(4-methyl-D-leucyl)-4,5-dihydro-1H-pyrazole-5-carboxamide, (5S)—N-[5-Chloro-2-(1H-tetrazol-1-yl)benzyl]-1-[(2R)-3-cyclopropyl-2-hydroxypropanoyl]-4,5-dihydro-1H-pyrazole-5-carboxamide, (5S)—N-[5-Chloro-2-(1H-tetrazol-1-yl)benzyl]-1-[(2R)-2-hydroxy-3,3-dimethylbutanoyl]-4,5-dihydro-1H-pyrazole-5-carboxamide, (5S)—N-[5-Chloro-2-(1H-tetrazol-1-yl)benzyl]-1-[(3-cyanophenyl)(hydroxy)acetyl]-4,5-dihydro-1H-pyrazole-5-carboxamide, (5S)—N-[5-Chloro-2-(1H-tetrazol-1-yl)benzyl]-1-[(2S)-2-(4-fluorophenyl)-2-hydroxyacetyl]-4,5-dihydro-1H-pyrazole-5-carboxamide,

[(1R)-2-[(5S)-5-[[5-Chloro-2-(tetrazol-1-yl)phenyl]methylcarbamoyl]-4,5-dihydropyrazol-1-yl]-1-(4-fluorophenyl)-2-oxo-ethyl]acetate, (1R)-2-[(5S)-5-{[5-Chloro-2-(1H-tetrazol-1-yl)benzyl]carbamoyl}-4,5-dihydro-1H-pyrazol-1-yl]-1-(4-fluorophenyl)-2-oxoethyl 3-methylbutanoate, (1R)-2-[(5S)-5-{[5-Chloro-2-(1H-tetrazol-1-yl)benzyl]carbamoyl}-4,5-dihydro-1H-pyrazol-1-yl]-1-(4-fluorophenyl)-2-oxoethyl butanoate, (1R)-2-[(5S)-5-{[5-Chloro-2-(1H-tetrazol-1-yl)benzyl]carbamoyl}-4,5-dihydro-1H-pyrazol-1-yl]-1-(4-fluorophenyl)-2-oxoethyl 2-methylpropanoate, (1R)-2-[(5S)-5-{[5-Chloro-2-(1H-tetrazol-1-yl)benzyl]carbamoyl}-4,5-dihydro-1H-pyrazol-1-yl]-1-(4-fluorophenyl)-2-oxoethyl pentanoate, (1R)-2-[(5S)-5-{[5-Chloro-2-(1H-tetrazol-1-yl)benzyl]carbamoyl}-4,5-dihydro-1H-pyrazol-1-yl]-1-(4-fluorophenyl)-2-oxoethyl propanoate, (1R)-2-[(5S)-5-{[5-Chloro-2-(1H-tetrazol-1-yl)benzyl]carbamoyl}-4,5-dihydro-1H-pyrazol-1-yl]-1-(4-fluorophenyl)-2-oxoethyl benzoate, (R)-2-((S)-5-(5-Chloro-2-(1H-tetrazol-1-yl)benzylcarbamoyl)-4,5-dihydro-1H-pyrazol-1-yl)-1-(4-fluorophenyl)-2-oxoethyl 3-(2,4-dimethyl-6-(propionyloxy)phenyl)-3-methylbutanoate, (3S)—N-[5-Chloro-2-(1H-tetrazol-1-yl)benzyl]-2-[(2R)-2-(4-fluorophenyl)-2-hydroxyacetyl]isoxazolidine-3-carboxamide, (3S)-2-(O-tert-Butyl-D-seryl)-N-[5-chloro-2-(1H-tetrazol-1-yl)benzyl]isoxazolidine-3-carboxamide, (3S)—N-[5-Chloro-2-(1H-tetrazol-1-yl)benzyl]-2-[(2,4-difluorophenyl)(hydroxy)acetyl]isoxazolidine-3-carboxamide, (3S)—N-[5-Chloro-2-(1H-tetrazol-1-yl)benzyl]-2-[(2,3-difluorophenyl)(hydroxy)acetyl]isoxazolidine-3-carboxamide, (3S)—N-[5-Chloro-2-(1H-tetrazol-1-yl)benzyl]-2-[(3,5-difluorophenyl)(hydroxy)acetyl]isoxazolidine-3-carboxamide, (3S)—N-[5-Chloro-2-(1H-tetrazol-1-yl)benzyl]-2-[(2-fluorophenyl)(hydroxy)acetyl] isoxazolidine-3-carboxamide, (3S)—N-[5-Chloro-2-(1H-tetrazol-1-yl)benzyl]-2-[hydroxy (3-methylphenyl)acetyl] isoxazolidine-3-carboxamide, (3S)—N-[5-Chloro-2-(1H-tetrazol-1-yl)benzyl]-2-[(2R)-2-hydroxyhexanoyl]isoxazolidine-3-carboxamide, (3S)—N-[5-Chloro-2-(1H-tetrazol-1-yl)benzyl]-2-[(2R)-2-hydroxy-5-methylhexanoyl]isoxazolidine-3-carboxamide, (3S)-2-[(2R)-3-tert-Butoxy-2-hydroxypropanoyl]-N-[5-chloro-2-(1H-tetrazol-1-yl)benzyl]isoxazolidine-3-carboxamide, (3S)—N-[5-Chloro-2-(1H-tetrazol-1-yl)benzyl]-2-[(2R)-2-cyclopentyl-2-hydroxyacetyl]isoxazolidine-3-carboxamide, (3S)—N-[5-Chloro-2-(1H-tetrazol-1-yl)benzyl]-2-[(2R)-2-cyclohexyl-2-hydroxyacetyl]isoxazolidine-3-carboxamide, (3S)—N-[5-Chloro-2-(1H-tetrazol-1-yl)benzyl]-2-[(2R)-2-hydroxy-3-(1-methylcyclopropyl)propanoyl] isoxazolidine-3-carboxamide, (3S)—N-[5-Chloro-2-(1H-tetrazol-1-yl)benzyl]-2-[(2R)-2-hydroxy-2-phenylacetyl] isoxazolidine-3-carboxamide, (3S)—N-[5-Chloro-2-(1H-tetrazol-1-yl)benzyl]-2-[(2R)-2-hydroxy-3,3-dimethylbutanoyl]isoxazolidine-3-carboxamide, (3S)—N-[5-Chloro-2-(1H-tetrazol-1-yl)benzyl]-2-[(2R)-2-hydroxy-4,4-dimethylpentanoyl]isoxazolidine-3-carboxamide,
(3S)—N-[5-Chloro-2-(1H-tetrazol-1-yl)benzyl]-2-[(2R)-2-hydroxy-3-phenylpropanoyl]isoxazolidine-3-carboxamide,
(3S)—N-[5-Chloro-2-(1H-tetrazol-1-yl)benzyl]-2-[(3-cyanophenyl)(hydroxy)acetyl]isoxazolidine-3-carboxamide,
(3S)—N-[5-Chloro-2-(1H-tetrazol-1-yl)benzyl]-2-[(2R)-2-hydroxy-2-phenylacetyl]pyrazolidine-3-carboxamide,
(3S)—N-[5-Chloro-2-(1H-tetrazol-1-yl)benzyl]-2-[(2-fluorophenyl)(hydroxy)acetyl]pyrazolidine-3-carboxamide,
(3S)—N-[5-Chloro-2-(1H-tetrazol-1-yl)benzyl]-2-[(2,4-difluorophenyl)(hydroxy)acetyl]pyrazolidine-3-carboxamide,
(3S)—N-[5-Chloro-2-(1H-tetrazol-1-yl)benzyl]-2-[(2R)-2-(4-fluorophenyl)-2-hydroxyacetyl]pyrazolidine-3-carboxamide,
(3S)—N-[5-Chloro-2-(1H-tetrazol-1-yl)benzyl]-2-[(4-hydroxy-3,4-dihydro-2H-chromen-4-yl)carbonyl]pyrazolidine-3-carboxamide,
(3S)—N-[5-Chloro-2-(1H-tetrazol-1-yl)benzyl]-2-[(2R)-2-hydroxy-4,4-dimethylpentanoyl]pyrazolidine-3-carboxamide,
(3S)—N-[5-Chloro-2-(1H-tetrazol-1-yl)benzyl]-2-[(2R)-2-cyclohexyl-2-hydroxyacetyl]pyrazolidine-3-carboxamide,
(3S)—N-[5-Chloro-2-(1H-tetrazol-1-yl)benzyl]-2-[(2R)-2-hydroxy-3-phenylpropanoyl]pyrazolidine-3-carboxamide or
(3S)—N-[5-Chloro-2-(1H-tetrazol-1-yl)benzyl]-2-[(2R)-2-hydroxy-3,3-dimethylbutanoyl]pyrazolidine-3-carboxamide, or a pharmaceutically acceptable salt or an enantiomer or a pharmaceutically acceptable salt of said enantiomer.

In another aspect of the present invention there is provided a compound of formula (X)

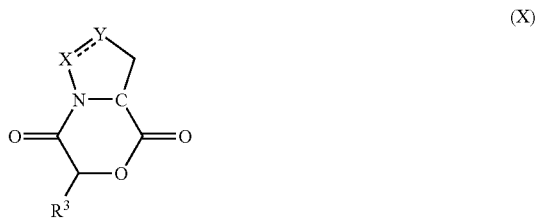

(X)

X is N, O or NH;
Y is $CH_2$ when X is O or NH, with X and Y connected via a single bond, or
Y is CH when X is N, with X and Y connected via a double bond;
$R^3$ is $C_{1-6}$ alkyl, $C_{3-6}$ cycloalkyl, a 5 or 6-membered heteroaromatic ring containing 1, 2 or 3 heteroatoms independently selected from O, S and N,
a 4-, 5- or 6-membered cycloheteroalkyl ring containing 1 or 2 heteroatoms independently selected from O, S and N, or $R^{12}$, wherein said $C_{1-6}$ alkyl, said $C_{3-6}$ cycloalkyl, said heteroaromatic ring and said cycloheteroalkyl ring are substituted by 0 or 1 substituents selected from $NH_2$, $NH(C_{1-4}$ alkyl), $N(C_{1-4}$ alkyl$)_2$, $C_3$ cycloalkyl, $R^6$ or $R^{12}$;
$R^6$ is $C_{1-6}$ alkoxy, wherein said $C_{1-6}$ alkoxy is substituted by 0, 1, 2, 3, 4 or 5 halogen; and
$R^{12}$ is phenyl, wherein said phenyl is substituted by 0, 1 or 2 substituents selected from halogen and $R^6$.

In yet another aspect of the present invention there is provided a compound of formula (XI)

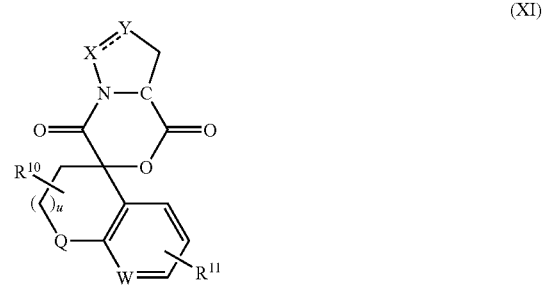

(XI)

X is N, O or NH;
Y is $CH_2$ when X is O or NH, with X and Y connected via a single bond,
or
Y is CH when X is N, with X and Y connected via a double bond;
Q is O or $CH_2$;
u is independently 0 or 1; and
$R^{10}$ is 0, 1 or 2 substituents selected from $C_{1-4}$ alkyl, halogen and $R^6$;
$R^{11}$ is 0, 1 or 2 substituents selected from $C_{1-4}$ alkyl, halogen and $R^6$;
$R^6$ is $C_{1-6}$ alkoxy, wherein said $C_{1-6}$ alkoxy is substituted by 0, 1, 2, 3, 4 or 5 halogen.

The present invention further provides a process for the preparation of a compound of formula (I) as defined above which comprises:

(A) reacting a compound of formula (II),

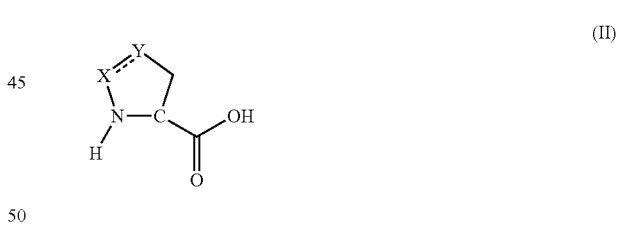

(II)

wherein X and Y are as defined in formula (I), or a derivative thereof that is protected at the amino group, with an amine of formula (III)

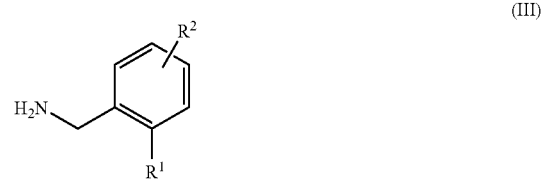

(III)

wherein $R^1$ and $R^2$ are as defined in formula (I) to deliver a compound of formula (IV), or a derivative thereof that is protected at the amino group, (B) reacting a compound of formula (IV),

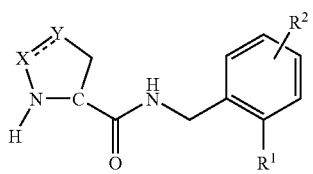
(IV)

wherein X, Y, R¹ and R² are as defined in formula (I), with a compound of formula (V)

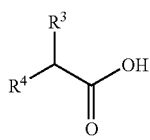
(V)

wherein $R^3$ is as hereinbefore defined and $R^4$ is OH, or a derivative thereof that is either protected at the hydroxy substituent or at both the hydroxy substituent and at the carboxylic acid, to deliver a compound of formula (I);

(C) reacting a compound of formula (IV),

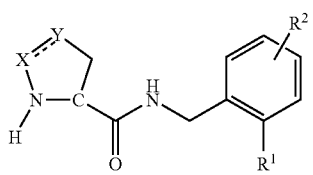
(IV)

wherein X, Y, R¹ and R² are as defined in formula (I), with a compound of formula (VI)

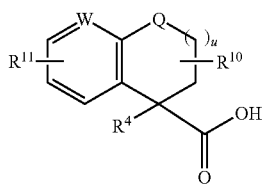
(VI)

wherein $R^{10}$, $R^{11}$, W, Q and u are as hereinbefore defined and $R^4$ is OH, or a derivative thereof that is either protected at the hydroxy substituent or at both the hydroxy substituent and at the carboxylic acid, to deliver a compound of formula (I);

(D) reacting a compound of formula (IV),

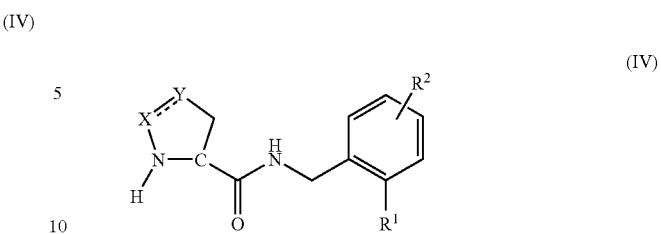
(IV)

wherein X, Y, R¹ and R² are as defined in formula (I), with a compound of formula (V)

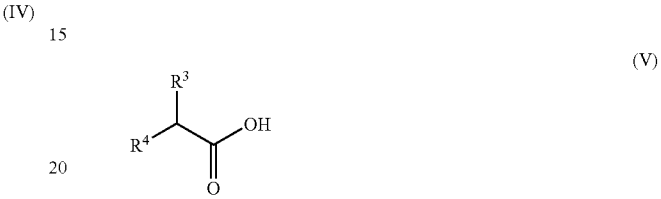
(V)

wherein $R^3$ is as hereinbefore defined and $R^4$ is NHR⁹, wherein $R^9$ is as hereinbefore defined, or a derivative thereof that is protected at the amino substituent, to deliver a compound of formula (I);

(E) reacting a compound of formula (IV),

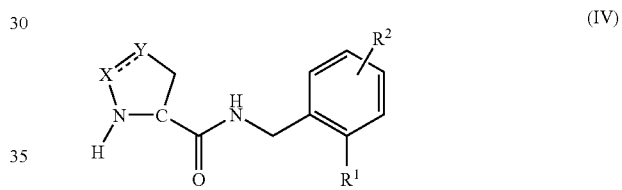
(IV)

wherein X, Y, R¹ and R² are as defined in formula (I), with a compound of formula (VI)

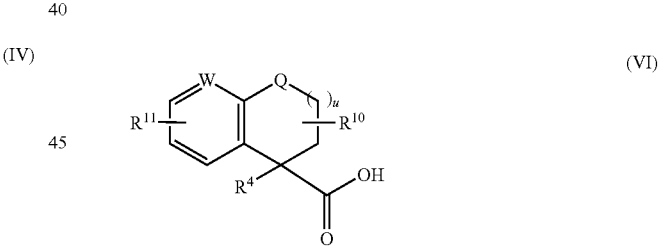
(VI)

wherein $R^{10}$, $R^{11}$, W, Q and u are as hereinbefore defined and $R^4$ is NHR⁹, wherein $R^9$ is as hereinbefore defined, or a derivative thereof that is protected at the amino substituent, to deliver a compound of formula (I);

(F) reacting a compound of formula (IV),

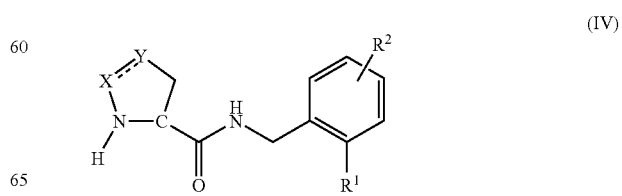
(IV)

wherein X, Y, R¹ and R² are as defined in formula (I), with a compound of formula (VII)

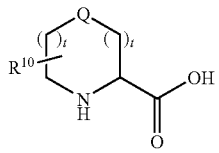
(VII)

wherein R¹⁰, Q and t are as hereinbefore defined, or a derivative thereof that is protected at the amino group, to deliver a compound of formula (I);

(G) reacting a compound of formula (II),

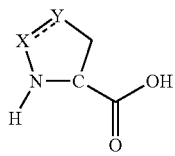
(II)

wherein X and Y are as defined in formula (I), or a derivative thereof that is protected at the carboxylic acid, with a compound of formula (V)

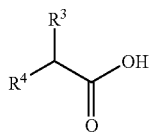
(V)

wherein R³ is as hereinbefore defined and R⁴ is OH, or a derivative thereof that is either protected at the hydroxy substituent or at both the hydroxy substituent and at the carboxylic acid, to deliver a compound of formula (VIII);

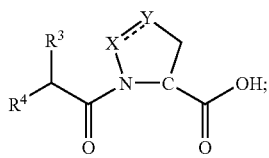
(VIII)

(H) reacting a compound of formula (II),

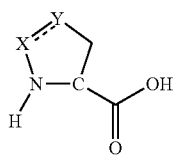
(II)

wherein X and Y are as defined in formula (I), or a derivative thereof that is protected at the carboxylic acid, with a compound of formula (VI)

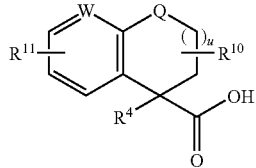
(VI)

wherein R¹⁰, R¹¹, W, Q and u are as hereinbefore defined and R⁴ is OH, or a derivative thereof that is either protected at the hydroxy substituent or at both the hydroxy substituent and at the carboxylic acid, to deliver a compound of formula (IX)

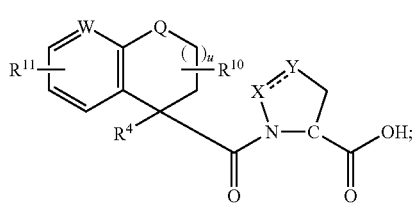
(IX)

(I) reacting a compound of formula (VIII), or a derivative thereof that is protected at the carboxylic acid,

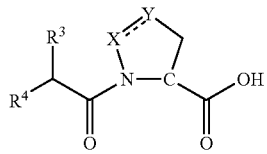
(VIII)

wherein X, Y and R³ is as hereinbefore defined and R⁴ is OH, or a derivative thereof that is protected at the OH group, to deliver a compound of formula (X)

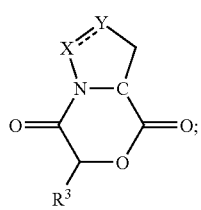
(X)

(J) reacting a compound of formula (IX), or a derivative thereof that is protected at the carboxylic acid,

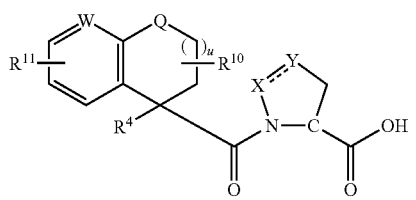
(IX)

wherein R¹⁰, R¹¹, X, Y, W, Q and u are as hereinbefore defined and R⁴ is OH, or a derivative thereof that is protected at the OH group, to deliver a compound of formula (XI)

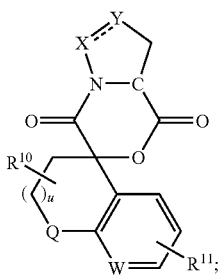

(K) reacting a compound of formula (X) or formula (XI), wherein $R^3$, $R^{10}$, $R^{11}$, X, Y, W, Q and u are as hereinbefore defined with a compound of formula (III), wherein $R^1$ and $R^2$ are as hereinbefore defined, to deliver a compound of formula (I);

(L) reacting a compound of formula (II),

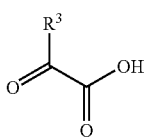

wherein X and Y are as defined in formula (I), or a derivative thereof that is protected at the carboxylic acid, with a compound of formula (XII)

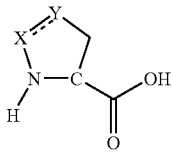

wherein $R^3$ is as hereinbefore defined, to deliver a compound of formula (XIII)

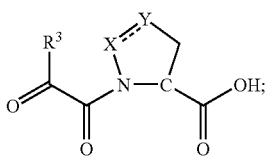

(M) reacting a compound of formula (XIII), wherein X, Y and $R^3$ are as hereinbefore defined, or a derivative thereof that is protected at the carboxylic acid, under reducing conditions to deliver a compound of formula (VIII)

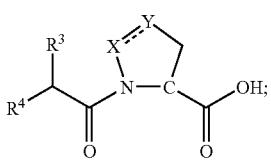

(N) reacting a compound of formula (XIV),

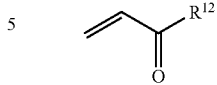

wherein $R^{12}$ is OH, alkoxy, aryloxy or $R^{13}$, wherein $R^{13}$ is a chiral auxiliary, e.g., 2,10-camphorsultam, 6,6-dimethyl-7,10-methylen-3-oxa-1-azaspiro[4.5]decan-2-one or 4-benzyl-2-oxazolidinone, with trimethylsilyldiazomethane to deliver a compound of formula (XV)

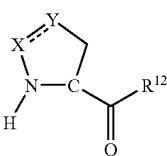

wherein Y is CH, X is N, $R^{12}$ is OH, alkoxy, aryloxy or $R^{13}$ and the bond between X and Y is a double bond.

(O) reacting a compound of formula (XVI),

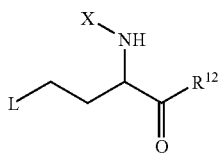

wherein $R^{12}$ is OH or alkoxy, L is Cl, Br, I or $OSO_2CF_3$ and X is O, N or a protected derivative thereof, in the presence of base to deliver a compound of formula (XV)

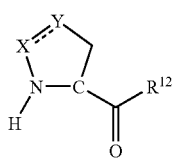

wherein Y is $CH_2$, X is N or O, $R^{12}$ is OH or alkoxy and the bond between X and Y is a single bond.

Processes (A)-(H) and (L) may be carried out using known procedures for preparation of amides from carboxylic acids, or analogously, e.g. as hereinafter described in the Examples. It may be carried out in a solvent, e.g. DCM, MeCN, $H_2O$, EtOAc or DMF, in the presence of an appropriate base, e.g. pyridine, DMAP, NMM, TEA, $NaHCO_3$, 2,4,6-collidine or DIPEA, and a suitable reagent, e.g. oxalyl chloride, cyanuric fluoride, EDC/HOBt, DCC/HOBt, HBTU, HATU, PyBOP, T3P or TBTU. The reaction temperature may be from 0° C. to 100° C., or at the reflux temperature of the solvent if <100° C., but conveniently room temperature.

Processes (I) and (J) may be carried out using known procedures for preparation of lactones, or analogously, e.g. as hereinafter described in the Examples. It may be carried out in an organic solvent, e.g. $CHCl_3$, benzene, toluene, ETOH or THF, in the presence of a suitable reagent, e.g. TsOH, MsOH, NaOH, pivaloyl chloride/TEA or DMAP/BOP. The reaction temperature may be from 0° C. to 100° C., or at the reflux temperature of the solvent if <100° C., but conveniently room temperature.

Process (K) may be carried out using known procedures for preparation of amides from lactones, or analogously, e.g. as hereinafter described in the Examples. It may be carried out in an organic solvent, e.g. DCM, THF or MeOH, in the presence of a suitable reagent, e.g. TEA. The reaction temperature may be from 0° C. to 100° C., or at the reflux temperature of the solvent if <100° C., but conveniently room temperature.

Process (M) may be carried out using known procedures for preparation of alcohols from ketones, or analogously, e.g. as hereinafter described in the Examples. It may be carried out in an organic solvent, e.g. THF, in the presence of a suitable reagent, e.g. $NaBH_4$, $Zn(BH_4)_2$, $Ph_2SiH_2$ in the presence of a suitable catalyst, e.g. $Rh(PPh_3)_3Cl$ or Rh(I)-2-(2-pyridyl)-4-carbomethoxy-1,3-thiazolidine, or, alternatively, in the presence of $H_2$ and a suitable catalyst, e.g. Ru/C, Rh-DIOP or Rh—CYDIOP. The reaction temperature may be from 0° C. to 100° C., or at the reflux temperature of the solvent if <100° C., but conveniently room temperature.

Process (N) may be carried out using known procedures for preparation of pyrazolines from olefins, or analogously, e.g. as hereinafter described in the Examples. It may be carried out in an organic solvent, e.g. methylene chloride, hexane or THF. The reaction temperature may be from −100° C. to 100° C., or at the reflux temperature of the solvent if <100° C., but conveniently room temperature.

Process (O) may be carried out using known procedures for preparation of pyrazolidines or isoxazolidines, or analogously, e.g. as hereinafter described in the Examples. It may be carried out in an organic solvent, e.g. THF, in the presence of a suitable reagent, e.g. NaHMDS, LiHMDS or tetrabutylammoniumfluoride. The reaction temperature may be from 0° C. to 100° C., or at the reflux temperature of the solvent if <100° C., but conveniently room temperature.

Processes used for hydrolyzing carboxylic esters to carboxylic acids may be carried out using known procedures, or analogously, e.g. as hereinafter described in the Examples. It may be carried out in a solvent, e.g. MeCN or $H_2O$ in the presence of an appropriate base, e.g. TEA or DIPEA, or a suitably acid, e.g. HCl, and optionally a suitable reagent, e.g. LiBr. The reaction temperature may be from 0° C. to 100° C., or at the reflux temperature of the solvent if <100° C., but conveniently room temperature.

Compounds of formula (II) and formula (XV) are either commercially available or may be prepared by known methods (e.g. *Tetrahedron Letters* 1997, 38, 4935-4938 (N—NH—CH$_2$); *J. Am. Chem. Soc.* 1997, 119, 8379-8380 (N—N═CH); *Helv. Chim. Acta* 1983, 66, 1241 (N—O—C)).

Compounds of formula (III) are either commercially available or may be prepared by known methods (e.g. *J. Med. Chem.* 2004, 47, 2995).

Compounds of formula (V), (VI), (VII), (XII) and (XIV) are either commercially available or may be prepared by known methods.

The protection and deprotection of functional groups is described in 'Protective Groups in Organic Synthesis', 2$^{nd}$ Ed, T. W. Greene and P. G. M. Wuts, Wiley-Interscience (1991) and 'Protecting Groups', P. J. Kocienski, Georg Thieme Verlag (1994).

A further embodiment of the invention encompasses pharmaceutically acceptable salts of the compounds of formula (I). Where the compound is sufficiently acidic, pharmaceutically-acceptable salts include, but are not limited to, an alkali metal salt for example sodium or potassium, an alkaline earth metal salt for example calcium or magnesium, an organic amine salt for example triethylamine, morpholine, N-methylpiperidine, N-ethylpiperidine, procaine, dibenzylamine, N,N-dibenzylethylamine or amino acids for example lysine. Where the compound is sufficiently basic, pharmaceutically acceptable salts include, but are not limited to, acid addition salts such as a hydrochloride, hydrobromide, phosphate, acetate, fumarate, maleate, tartrate, citrate, oxalate, methanesulfonate or p-toluenesulfonate salt.

There may be more than one cation or anion depending on the number of charged functions and the valency of the cations or anions.

For a review on suitable salts, see Berge et al., *J. Pharm. Sci.*, 66, 1-19 (1977).

The compounds of formula (I) may be administered in the form of a prodrug which is broken down in the human or animal body to give a compound of the formula (I). Certain compounds of formula (I) may themselves act as prodrugs of other compounds of formula (I). Prodrugs of formula (I) may display improved physicochemical, biopharmaceutical or pharmacokinetic properties. Examples of prodrugs include in vivo hydrolysable esters of a compound of the formula (I).

An in vivo hydrolysable (or cleavable) ester of a compound of the formula (I) that contains a carboxy or a hydroxy group is, for example, a pharmaceutically acceptable ester which is hydrolysed in the human or animal body to produce the parent acid or alcohol. For examples of ester prodrugs derivatives, see: *Curr. Drug. Metab.* 2003, 4, 461.

Various other forms of prodrugs are known in the art. For examples of prodrug derivatives, see: Rautio, J. et al. *Nature Reviews Drug Discovery* 2008, 7, 255 and references cited therein.

Medical and Pharmaceutical Use

The compounds of the invention are thus expected to be useful in those conditions where inhibition of thrombin is beneficial (as determined by reference to a clinically relevant end-point, e.g. conditions, such as thrombo-embolisms, where inhibition of thrombin is required or desired, and/or conditions where anticoagulant therapy is indicated), including the following:

The treatment and/or prophylaxis of thrombosis and hypercoagulability in blood and/or tissues of animals including man. It is known that hypercoagulability may lead to thrombo-embolic diseases. Conditions associated with hypercoagulability and thrombo-embolic diseases are usually designated as thrombophilia conditions. These conditions include, but are not limited to, inherited or acquired activated protein C resistance, such as the factor V-mutation (factor V Leiden), inherited or acquired deficiencies in antithrombin III, protein C, protein S, protein Z, heparin cofactor II, and conditions with increased plasma levels of the coagulation factors such as caused by the prothrombin G20210A mutation. Other conditions known to be associated with hypercoagulability and thrombo-embolic disease include circulating antiphospholipid antibodies (Lupus anticoagulant), homocysteinemi, heparin induced thrombocytopenia and defects in fibrinolysis, as well as coagulation syndromes (e.g. disseminated intravascular coagulation (DIC)) and vascular injury in general (e.g. due to trauma or surgery). Furthermore, low physical activity, low cardiac output or high age are known to increase the risk of thrombosis and hypercoagulability may be just one of several factors underlying the increased risk. These conditions include, but are not limited to, prolonged bed rest, prolonged air travelling, hospitalisation for an acute medical disorder such as cardiac insufficiency or respiratory insufficiency. Further conditions with increased risk of thrombosis with hypercoagulability as one component are pregnancy and hormone treatment (e.g. oestrogen).

The treatment of conditions where there is an undesirable excess of thrombin without signs of hypercoagulability, for example in neurodegenerative diseases such as Alzheimer's disease, in the progression and/or prevention of atherosclerosis and in growth and spreading of cancer.

Particular disease states which may be mentioned include the therapeutic and/or prophylactic treatment of venous thrombosis (e.g. deep venous thrombosis, DVT) and pulmonary embolism, arterial thrombosis (e.g. in myocardial infarction, unstable angina and acute coronary syndrome, thrombosis-based stroke and peripheral arterial thrombosis), and systemic embolism (which may lead to stroke) usually from the atrium during atrial fibrillation (e.g. non-valvular or valvular atrial fibrillation) or from the left ventricle after transmural myocardial infarction, or caused by congestive heart failure; prophylaxis of re-occlusion (i.e. thrombosis) after thrombolysis, percutaneous trans-luminal interventions (PTI) and coronary bypass operations; the prevention of thrombosis after microsurgery and vascular surgery in general, organ transplantation and plastic surgery.

Further indications include the therapeutic and/or prophylactic treatment of disseminated intravascular coagulation caused by bacteria, multiple trauma, intoxication or any other mechanism; anticoagulant treatment when blood is in contact with foreign surfaces in the body such as vascular grafts, vascular stents, vascular catheters, mechanical and biological prosthetic valves or any other medical device; and anticoagulant treatment when blood is in contact with medical devices outside the body such as during cardiovascular surgery using a heart-lung machine or in haemodialysis; the therapeutic and/or prophylactic treatment of idiopathic and adult respiratory distress syndrome, pulmonary fibrosis following treatment with radiation or chemotherapy, chronic obstructive pulmonary disease, septic shock, septicaemia, inflammatory responses, which include, but are not limited to, edema, acute or chronic atherosclerosis such as coronary arterial disease and the formation of atherosclerotic plaques, cardiac insufficiency, cerebral arterial disease, cerebral infarction, cerebral thrombosis, cerebral embolism, peripheral arterial disease, ischemia, angina (including unstable angina), reperfusion damage, restenosis after percutaneous trans-luminal interventions (PTI) and coronary artery bypass surgery.

Compounds of the invention that inhibit trypsin and/or thrombin may also be useful in the treatment of pancreatitis.

The compounds of the invention are thus indicated both in the therapeutic and/or prophylactic treatment of these conditions.

According to one aspect of the invention there is thus provided the use of a compound of formula (I) in therapy.

According to a further aspect of the invention there is thus provided the use of a compound of formula (I) in anticoagulant therapy.

According to still a further aspect of the invention there is thus provided the use of a compound of formula (I) in the treatment of a condition where inhibition of thrombin is beneficial.

According to still a further aspect of the invention there is thus provided the use of a compound of formula (I) in the treatment and prevention of thromboembolic disorders.

According to still a further aspect of the invention there is thus provided the use of a compound of formula (I) for the manufacture of a medicament for the treatment of a condition where inhibition of thrombin is beneficial.

According to still a further aspect of the invention there is thus provided the use of a compound of formula (I) for the manufacture of a medicament for the treatment and prevention of thromboembolic disorders.

According to still a further aspect of the invention there is thus provided a method of treatment of a condition where inhibition of thrombin is beneficial, which method comprises administration of a therapeutically effective amount of a compound of formula (I) to a person suffering from, or susceptible to, such a condition.

According to still a further aspect of the invention there is thus provided a method of treatment and prevention of thromboembolic disorders, which method comprises administration of a therapeutically effective amount of a compound of formula (I) to a person suffering from, or susceptible to, thrombophilia conditions.

The compounds of the invention have the advantage that they may be more efficacious, be less toxic, be more selective (e.g. for inhibiting thrombin over other serine proteases, in particular trypsin and those involved in haemostasis), be more potent, produce fewer side effects, be more easily absorbed, and/or have a better pharmacokinetic profile (e.g. higher oral bioavailability and/or lower clearance), than compounds known in the prior art.

Pharmaceutical Formulation

According to a further aspect of the present invention, there is provided a method of treatment of a condition where inhibition of thrombin is required which method comprises administration of a therapeutically effective amount of a compound of the invention to a person suffering from, or susceptible to, such a condition.

The compounds of the invention will normally be administered orally, intravenously, subcutaneously, buccally, rectally, dermally, nasally, tracheally, bronchially, by any other parenteral route or via inhalation, in the form of pharmaceutical preparations comprising a compound of the invention either as a free base, or a pharmaceutically acceptable non-toxic organic or inorganic acid addition salt, in a pharmaceutically acceptable dosage form.

Preferred route of administration of compounds of the invention is oral.

Depending upon the disorder and patient to be treated and the route of administration, the compositions may be administered at varying doses.

The compounds of the invention may also be combined and/or co-administered with any antithrombotic agent(s) with a different mechanism of action, such as one or more of the following: the anticoagulants unfractionated heparin, low molecular weight heparin, other heparin derivatives, synthetic heparin derivatives (e.g. fondaparinux), vitamin K antagonists, synthetic or biotechnological inhibitors of other coagulation factors than thrombin (e.g. synthetic FXa, FVIIa, FIXa and FXIa inhibitors, and rNAPc2), the antiplatelet agents acetylsalicylic acid and dipyridamole, thromboxane receptor and/or synthetase inhibitors, fibrinogen receptor antagonists, prostacyclin mimetics, phosphodiesterase inhibitors, ADP-receptor ($P2X_1$, $P2Y_1$, $P2Y_{12}$ [e.g. ticlopidine, clopidogrel, cangrelor, satigrel and AZD6140]) antagonists, inhibitors of phosphoinositide 3-kinase beta or gamma, inhibitors of carboxypeptidase U (CPU or TAFIa) and inhibitors of plasminogen activator inhibitors (PAI-1, e.g. SCH530348 and E-5555).

The compounds of the invention may further be combined and/or co-administered with thrombolytics such as one or more of tissue plasminogen activator (natural, recombinant or modified), streptokinase, urokinase, prourokinase, anisoylated plasminogen-streptokinase activator complex (AP- SAC), animal salivary gland plasminogen activators, and the like, in the treatment of thrombotic diseases, in particular myocardial infarction.

According to a further aspect of the invention there is thus provided a pharmaceutical formulation comprising a compound of formula (I), in admixture with at least one pharmaceutically acceptable adjuvant, diluent or carrier.

Suitable daily doses of the compounds of the invention in therapeutic treatment of humans are about 0.001-100 mg/kg body weight at peroral administration and 0.001-50 mg/kg body weight at parenteral administration.

For the avoidance of doubt, as used herein, the term "treatment" includes therapeutic and/or prophylactic treatment.

EXAMPLES

The invention will now be further explained by reference to the following examples.

In the examples, high resolution mass spectra were recorded on a Micromass LCT mass spectrometer equipped with an electrospray interface (LC-HRMS). $^1$H NMR measurements were performed on Varian UNITY plus 400, 500 and 600 spectrometers, operating at $^1$H frequencies of 400, 500 and 600 MHz respectively. Chemical shifts are given in ppm with the solvent as internal standard. $(CH_3)_2SO^*$ of some reported NMR spectra refer to solutions that are taken from a concentrated sample dissolved in $(CH_3)_2SO$ and diluted with $(CD_3)_2SO$. Since a substantial amount of $(CH_3)_2SO$ is present in the sample, first a pre-scan is run and analysed to automatically suppress the $(CH_3)_2SO$ (2.54 ppm) and $H_2O$ (3.3 ppm) peaks. Thus the intensity of peaks that reside in these areas around 3.3 ppm and 2.54 ppm are altered. Because of this some signals from the compound around these frequencies may have been omitted and the omitted area is indicated in the specific Examples. Flash chromatography separations were performed using Merck Silica gel 60 (0.063-0.200 mm). The compounds named below were named using ACD/Name 9.04 from ACD/Labs.

The following abbreviations are used:

| | |
|---|---|
| DMF | Dimethylformamide |
| HATU | O-(7-Azobenzotriazol-1-yl)-1,1,3,3-tetramethyluronium hexafluorophosphate |
| PyBOP | Benzotriazol-1-yloxytripyrrolidinophosphonium hexafluorophosphate |
| T3P | Propylphosphonic anhydride |
| TBTU | O-Benzotriazolyl tetramethylisouronium tetrafluoroborate |
| EDC | 1-(3-Dimethylaminopropyl)-3-ethylcarbodiimide |
| DMAP | 4-(Dimethylamino)pyridine |
| NMM | N-Methylmorpholine |
| TEA | Triethylamine |
| DCM | Dichloromethane |
| DCC | Dicyclohexylcarbodiimide |
| BOP | Benzotriazol-1-yloxytris(dimethylamino)phosphonium hexafluorophosphate |
| HBTU | O-(Benzotriazol-1-yl)-N,N,N',N'-tetramethyluronium hexafluorophosphate |
| HATU | O-(7-Azobenzotriazol-1-yl)-N,N,N',N'-tetramethyluronium hexafluorophosphate |
| HOBt | 1-Hydroxybenzotriazole |
| HOAT | 1-Hydroxy-7-azabenzotriazole |
| DIPEA | N,N-Diisopropylethylamine |
| DIOP | Phosphine, [(2,2-dimethyl-1,3-dioxolane-4,5-diyl)bis(methylene)]bis[diphenyl-, trans- |
| CYDIOP | Phosphine, [(2,2-dimethyl-1,3-dioxolane-4,5-diyl)bis(methylene)]bis[dicyclohexyl-, trans- |
| NMP | 1-N-Methyl-2-pyrrolidinone |
| TBME | tert-Butyl methyl ether |

Example 1

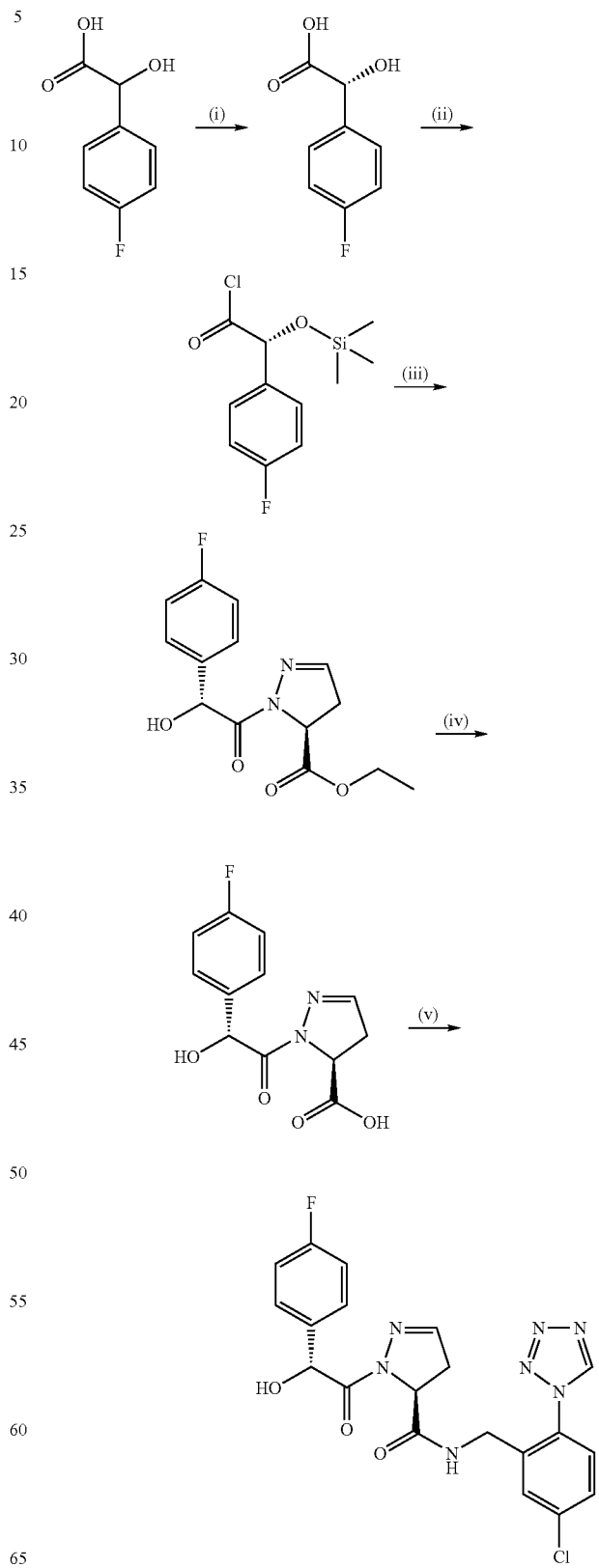

(5S)—N-[5-Chloro-2-(1H-tetrazol-1-yl)benzyl]-1-[(2R)-2-(4-fluorophenyl)-2-hydroxyacetyl]-4,5-dihydro-1H-pyrazole-5-carboxamide

(i) (2R)-(4-Fluorophenyl)(hydroxy)acetic acid

The reaction was performed in a 1 L reactor under an atmosphere of nitrogen with 200 rpm stirring. 2-(4-Fluorophenyl)-2-hydroxyacetic acid (139 g, 816.98 mmol) was charged into the reactor. Ethanol (800 mL) was added which resulted in a turbid mixture. The mixture was heated to reflux with a ramp of 1° C./min. (R)-(+)-1-phenylethylamine (68.5 mL, 531.04 mmol) was then added within 5 minutes. The clear homogenous solution was then allowed to slowly cool to 60° C. with a ramp of 1° C./min. When that temperature was reached, seeds of 95:5 diastereomeric purity was added (~100 mg). Crystallisation now slowly initiated. The temperature was ramped down to 20° C. with 0.5° C./min. When that temperature was reached the mixture was allowed to stir for another 2 hours. The mixture was then filtrated. This furnished crystals of the ammonium salt (95 g). This salt was then re-crystallised from ETOH (99.5%, 800 mL) using the following procedure: In a 1 L reactor and under an atmosphere of nitrogen, the salt obtained above was charged into the reactor. EtOH (800 mL) was added (a suspension was obtained) and the temperature was then increased to reflux with a ramp of 1° C./min. When all salt was dissolved, the temperature was ramped down with 1° C./min-->65° C. When that temperature was reached (clear homogenous solution), seeding crystals were added (approximately 0.5 g was added). Crystallization initiated immediately but very slowly. The temperature was then ramped down to 20° C. with 0.5° C./min. The mixture was then stirred (200 rpm) over night. After filtration and drying in vacuo, 67.9 g of the salt was obtained. Chiral HPLC analysis of the free acid of the salt showed an enantiomeric excess of 95.2% (97.6:2.4 er). The salt was recrystallized one more time from ETOH (99.5%, 500 mL) using the same procedure as described above but the mixture was only allowed to stir for 2 hours at room temperature instead of stirring over night. After filtration and drying, 56.3 g of crystals of the ammonium salt were obtained. Chiral HPLC analysis of the free acid showed an enantiomeric excess of 99.1%.

The ammonium salt above was then partitioned between methyl t-butyl ether (400 mL) and 1M HCl (aq., 300 mL). The aqueous phase was extracted with TBME (2×100 mL). The pooled organic phase was washed with water (100 mL) and then dried (MgSO$_4$) and concentrated. This furnished the title compound as a solid (32.5 g).

(ii) (2R)-(4-Fluorophenyl)[(trimethylsilyl)oxy]acetyl chloride

To a 0° C. solution of (2R)-(4-fluorophenyl)(hydroxy)acetic acid (20 g, 117.55 mmol), DMAP (0.718 g, 5.88 mmol), and pyridine (19.93 mL, 246.86 mmol) in dichloromethane (250 mL) was slowly (10 min) added chlorotrimethylsilane (30.6 mL, 240.98 mmol). The mixture was stirred under ice-cooling for 15 minutes and then at room temperature over night. The mixture was then cooled in an ice-bath and DMF (0.211 mL, 2.74 mmol) was added followed by the slow (15 min) addition of oxalylchloride (10.25 mL, 121.08 mmol). The suspension was stirred at 0° C. for 1 hour and for 30 minutes at room temperature. The mixture was then used as such in the next step. The yield of (2R)-(4-fluorophenyl)[(trimethylsilyl)oxy]acetoyl chloride is assumed to be 100%.

(iii) (Alternative 1) Ethyl (5S)-1-[(2R)-2-(4-fluorophenyl)-2-hydroxyacetyl]-4,5-dihydro-1H-pyrazole-5-carboxylate Under an atmosphere of nitrogen and on ice-cooling, ethyl acrylate (13.00 mL, 120 mmol) was dissolved in heptane (60 mL) and toluene (60 mL). Trimethylsilyldiazomethane (2M in hexanes, 60.0 mL, 120.00 mmol) was added. The solution was then allowed to reach room temperature and was stirred for 1.5 hour. The mixture was then concentrated under reduced pressure at 30° C. This furnished the crude intermediate cycloadduct which was used without further purification. Under an atmosphere of nitrogen under ice-cooling, to a solution of (2R)-(4-fluorophenyl)[(trimethylsilyl)oxy]acetoyl chloride (30.7 g, 117.7, mmol, see (ii) in dichloromethane (250 mL) was slowly (5 minutes) added the crude cycloadduct from above. The mixture was then allowed to reach room temperature and was stirred for 2 hours. LC/MS analysis of the crude mixture showed the correct product and one byproduct where the trimethylsilyl-group still remained intact. Water (300 mL) was added. The aqueous phase was extracted with CH$_2$Cl$_2$ (100 mL). The combined organic layers were concentrated to give a viscous oil (45 g). To this was then added Me-THF (100 mL) and TFA (44.6 mL, 600.00 mmol). The mixture was heated to 78° C. and was stirred over night. Water (200 mL) was added and the mixture was then allowed to stir vigorously for 15 minutes. EtOAc (300 mL) was added, the phases separated and the organic phase was concentrated. The crude diastereomeric mixture was then purified through silica gel chromatography using an eluent of 20-60% EtOAc in heptane as eluent. Pure fractions containing the desired diastereomer were collected and concentrated. Recrystallization from hot EtOAc/heptane (30/70, 200 mL) furnished the desired compound as a solid (8.9 g, 25% yield). $^1$H NMR (600 MHz, CDCl$_3$) δ 1.29 (t, 3H), 2.91 (ddd, 1H), 3.16 (ddd, 1H), 4.12 (d, 1H), 4.21-4.27 (m, 2H), 4.70 (dd, 1H), 5.72 (d, 1H), 6.88-6.90 (m, 1H), 6.97-7.01 (2H), 7.39-7.43 (m, 2H).

(iii) (Alternative 2) Ethyl (5S)-1-[(2R)-2-(4-fluorophenyl)-2-hydroxyacetyl]-4,5-dihydro-1H-pyrazole-5-carboxylate Under an atmosphere of nitrogen, ethyl acrylate (288 g, 2877 mmol) was dissolved in dichloromethane (4000 mL) at 20° C. with a stirring rate of 150 rpm. Trimethylsilyldiazomethane (2M in hexanes, 1150 mL, 2301 mmol) was added over a period of 30 min, after which the mixture was stirred at 20° C. for 19.5 h. After cooling to –30° C., trifluoroacetic acid (443 mL, 5752 mmol) was slowly added aver a period of 35 min. A crude mixture of (R)-2-(4-fluorophenyl)-2-(trimethylsilyloxy)acetyl chloride (600 g, 2301 mmol) in dichloromethane (4000 ml) was slowly added during 110 min, during which time the temperature was allowed to raise to 20° C. The mixture was stirred at 20° C. for 45 min after which EtOH (500 mL) and water (500 mL) were added in one portion. The mixture was stirred at 200 rpm for 50 min, water (2500 mL) was added, stirred 5 minutes at 200 rpm, then the layers were allowed to separate for 10 minutes.

The aqueous layer (4 L) was separated from the organic one (10.5 L), and to the organic layer was added a NaHCO3 solution (aq., 8%, 2.5 L). The mixture was stirred 10 minutes at 200 rpm after which the organic layer (V=9.75 L) was separated from the aqueous one (3000 mL). The crude product in the CH$_2$Cl$_2$ solution was concentrated in vacuo at 40° C. for 15 h. EtOAc (2000 mL) and heptane (1000 mL) were added to the solid and the resulting mixture was heated to reflux. Another 1000 mL of heptane was added after which seeding crystals (200 mg) of (5S)—N-[5-chloro-2-(1H-tetrazol-1-yl)benzyl]-1-[(2R)-2-(4-fluorophenyl)-2-hydroxyacetyl]-4,5-dihydro-1H-pyrazole-5-carboxamide was added, resulting in immediate crystallization. The stirring rate was set at 100 rpm and the temperature was ramped down to 20° C. with 1° C./min and the mixture was then stirred over night. The mixture was filtrated through a P3 filter and the filter cake was washed with EtOAc/heptane (50/50, 3×300 ml). The solid was then dried in vacuo to give the title compound (345 g, 51% yield).

(iv) (5S)-1-[(2R)-2-(4-Fluorophenyl)-2-hydroxyacetyl]-4,5-dihydro-1H-pyrazole-5-carboxylic acid To a solution of acetonitrile (70 mL), water (1.5 mL) and LiBr (12.69 g, 146.12 mmol) was added ethyl (5S)-1-[(2R)-2-(4-fluorophenyl)-2-hydroxyacetyl]-4,5-dihydro-1H-pyrazole-5-carboxylate (8.6 g, 29.22 mmol) followed by triethylamine (10.13 mL, 73.06 mmol). The homogenous clear solution was then stirred at room temperature over night. EtOAc (200 mL) and 1M HCl (aq., 150 mL) were added. The aqueous phase was extracted with EtOAc (100 mL). The pooled organic layers were then concentrated. This furnished 7.2 g of the desired acid as a solid. The pooled aqueous layers was extracted with EtOAc (2×50 mL), followed by washing of the combined organic layers with water (50 mL), an additional 0.42 g product was isolated. Total yield 98%. $^1$H NMR [400 MHz, (CD$_3$)$_2$SO] δ 2.86 (ddd, 1H), 3.23 (ddd, 1H), 4.53 (dd, 1H), 5.71-5.77 (m, 2H), 7.07-7.15 (m, 3H), 7.36-7.42 (m, 2H), 12.97 (s, br, 1H).

(v) (5S)—N-[5-Chloro-2-(1H-tetrazol-1-yl)benzyl]-1-[(2R)-2-(4-fluorophenyl)-2-hydroxyacetyl]-4,5-dihydro-1H-pyrazole-5-carboxamide In an open vessel, tert-butyl 5-chloro-2-(1H-tetrazol-1-yl)benzylcarbamate (14 g, 45.20 mmol, prepared as described in *J. Med. Chem.* 2004, 47, 2995, was suspended in acetonitrile (80 mL). HCl (6 M aqueous solution, 37.7 mL, 225.99 mmol) was added and the mixture was then stirred at room temperature for 4 hours. Water (200 mL) and TBME (100 mL) were added. To the aqueous phase and under ice-cooling was added EtOAc (200 mL) followed by slow addition of 2 M NaOH (aq., 130 mL). The organic phase was then washed with water (100 mL). To the EtOAc solution (220 mL) containing the crude (5-chloro-2-(1H-tetrazol-1-yl)phenyl)methanamine was then added (5S)-1-[(2R)-2-(4-fluorophenyl)-2-hydroxyacetyl]-4,5-dihydro-1H-pyrazole-5-carboxylic acid (7.53 g, 28.28 mmol) followed by the addition of N-methylmorpholine (4.66 mL, 42.43 mmol). To this clear homogenous solution was then added TBTU (10.90 g, 33.94 mmol) in one portion. The mixture was then stirred at room temperature over night. The precipitate formed was filtrated and then washed with TBME (100 mL). After drying in vacuo, the desired compound was obtained as a solid (7.65 g, 59%). The mother liquor was diluted with EtOAc and washed with Na$_2$CO$_3$ (aq., sat), water and 1 M HCl (aq.). Crystallization from CH$_3$CN/water gave 4.59 g of the title compound. Total yield 88%. $^1$H NMR (600 MHz, CD$_3$CN) δ 2.93 (ddd, 1H), 3.10 (ddd, 1H), 4.15-4.19 (m, 2H), 4.25 (dd, 1H), 4.60 (dd, 1H), 5.73-5.76 (m, 1H), 6.97-6.99 (m, 1H), 7.07-7.10 (m, 2H), 7.28-7.30 (m, 1H), 7.42-7.46 (m, 3H), 7.54-7.56 (m, 1H), 7.71 (d, 1H), 9.20 (s, 1H).

Examples 2-22 were prepared in a manner analogous to Example 1 described above using the appropriate starting materials.

Example 2

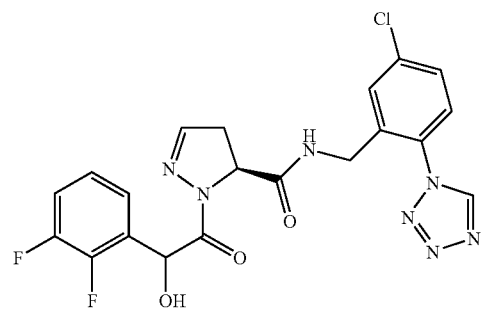

(5S)—N-[5-Chloro-2-(1H-tetrazol-1-yl)benzyl]-1-[(2,3-difluorophenyl)(hydroxy)acetyl]-4,5-dihydro-1H-pyrazole-5-carboxamide $^1$H NMR (400 MHz, CD$_3$OD) for the most potent isomer: δ 9.55 (s, 1H), 7.75 (d, 1H), 7.56 (dd, 1H), 7.49 (d, 1H), 7.22-7.13 (m, 2H), 7.13-7.06 (m, 1H), 6.95 (br. t, 1H), 6.06 (s, 1H), 4.64 (dd, 1H), 4.30 (d, 1H), 4.24 (d, 1H), 3.21-3.08 (m, 1H), 2.90-2.82 (m, 1H), HRMS (ESI) calculated for C$_{20}$H$_{16}$ClF$_2$N$_7$O$_3$ 476.1049 (M+H)$^+$. found 476.1050.

Example 3

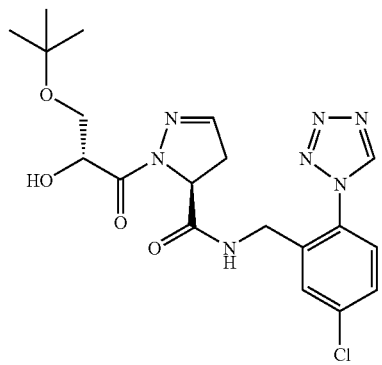

(5S)-1-[(2R)-3-tert-Butoxy-2-hydroxypropanoyl]-N-[5-chloro-2-(1H-tetrazol-1-yl)benzyl]-4,5-dihydro-1H-pyrazole-5-carboxamide $^1$H NMR (500 MHz, CDCl$_3$): δ 9.03 (s, 1H), 7.92 (br. t, 1H), 7.59 (d, 1H), 7.47 (dd, 1H), 7.28 (d, 1H), 7.06 (s, 1H), 4.90 (d, 1H), 4.89 (dd, 1 h), 4.33-4.21 (m, 2H), 3.69-3.62 (m, 2H), 3.65-3.58 (m, 1H), 3.07-2.98 (m, 1H), 1.13 (s, 9H), HRMS (ESI) calculated for $C_{19}H_{24}ClN_7O_4$ 450.1660 (M+H)$^+$. found 450.1680.

Example 4

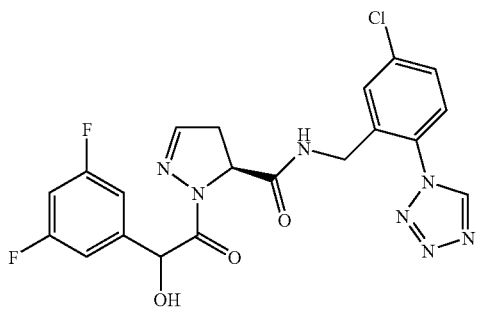

(5S)—N-[5-Chloro-2-(1H-tetrazol-1-yl)benzyl]-1-[(3,5-difluorophenyl)(hydroxy)acetyl]-4,5-dihydro-1H-pyrazole-5-carboxamide $^1$H NMR (400 MHz, CDCl$_3$): δ 8.96 (s, 1H), 7.67 (br. t, 1H), 7.63 (d, 1H), 7.48 (dd, 1H), 7.29 (d, 1H), 7.04 (br., 1H), 7.00-6.94 (m, 2H), 6.75-6.68 (m, 1H), 5.79 (d, 1H), 4.76 (dd, 1H), 4.29 (d, 2H), 4.15 (d, 1H), 3.60-3.52 (m, 1H), 3.03-2.93 (m, 1H), HRMS (ESI) calculated for $C_{20}H_{16}ClF_2N_7O_3$ 476.1049 (M+H)$^+$. found 476.1019.

Example 5

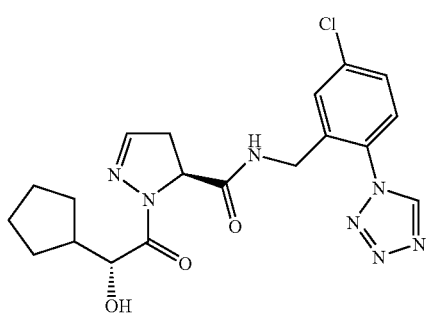

(5S)—N-[5-Chloro-2-(1H-tetrazol-1-yl)benzyl]-1-[(2R)-2-cyclopentyl-2-hydroxyacetyl]-4,5-dihydro-1H-pyrazole-5-carboxamide $^1$H NMR (600 MHz, CDCl$_3$): δ ppm 8.99 (s, 1H), 7.88 (br. s., 1H), 7.59 (d, 1H), 7.46 (dd, 1H), 7.30-7.25 (m, 1H), 7.06 (s, 1H), 4.86 (dd, 1H), 4.73 (dd, 1H), 4.27 (d, 2H), 3.64 (ddd, 1H), 3.16 (d, 1H), 3.03 (dd, 1H), 2.28-2.17 (m, 1H), 1.71-1.60 (m, 3H), 1.56-1.40 (m, 5H).

Example 6

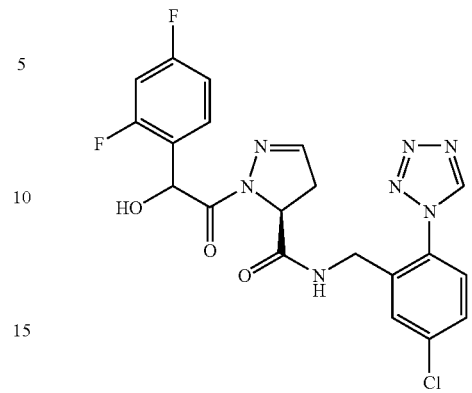

(5S)—N-[5-Chloro-2-(1H-tetrazol-1-yl)benzyl]-1-[(2,4-difluorophenyl)(hydroxy)acetyl]-4,5-dihydro-1H-pyrazole-5-carboxamide $^1$H NMR (500 MHz, CD$_3$CN) for the most potent isomer: δ 9.23 (s, 1H), 7.73 (d, 1H), 7.57 (dd, 1H), 7.48 (d, 1H), 7.40 (q, 1H), 7.33 (bt, 1H), 6.93-7.01 (m, 3H), 5.89 (d, 1H), 4.68 (dd, 1H), 4.17-4.31 (m, 3H), 3.12 (dd, 1H), 2.95 (dd, 1H). HRMS (ESI) calculated for $C_{20}H_{17}ClF_2N_7O_3$ 476.1049 (M+H)$^+$. found 476.1042.

Example 7

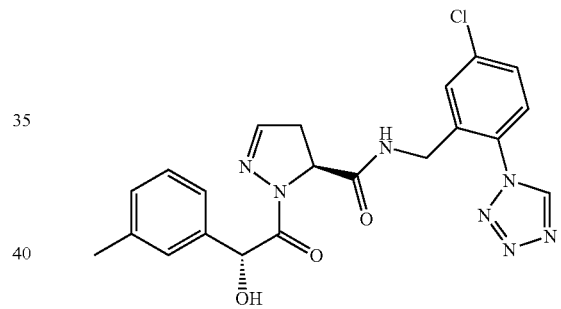

(5S)—N-[5-Chloro-2-(1H-tetrazol-1-yl)benzyl]-1-[(2R)-2-hydroxy-2-(3-methylphenyl)acetyl]-4,5-dihydro-1H-pyrazole-5-carboxamide $^1$H NMR (500 MHz, CDCl$_3$) for the most potent isomer: δ 9.00 (s, 1H), 7.83 (t, 1H), 7.62 (d, 1H), 7.46 (dd, 1H), 7.27-7.16 (m, 4H), 7.11-7.07 (m, 1H), 6.95 (s, 1H), 5.77 (s, 1H), 4.74 (dd, 1H), 4.28 (d, 2H), 4.02 (br., 1H), 3.49 (dd, 1H), 2.91 (m, 1H), 2.32 (s, 3H), HRMS (ESI) calculated for $C_{21}H_{20}ClN_7O_3$ 454.1394 (M+H)$^+$. found 454.1407.

Example 8

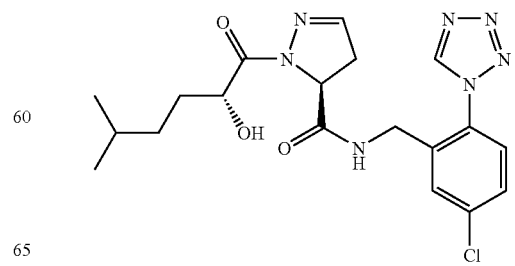

(5S)—N-[5-Chloro-2-(1H-tetrazol-1-yl)benzyl]-1-[(2R)-2-hydroxy-5-methylhexanoyl]-4,5-dihydro-1H-pyrazole-5-carboxamide $^1$H NMR (500 MHz, CDCl$_3$): δ 9.01 (s, 1H), 7.86 (br. t, 1H), 7.60 (d, 1H), 7.47 (dd, 1H), 7.29 (d, 1H), 7.07 (s, 1H), 4.87 (dd, 1H), 4.74 (br. t, 1H), 4.28 (d, 2H), 3.61 (dd, 1H), 3.20 (d, 1H), 3.06 (dd, 1H), 1.78-1.69 (m, 1H), 1.61-1.50 (m, 2H), 1.40-1.29 (m, 2H), 0.89 (t, 6H), HRMS (ESI) calculated for C$_{19}$H$_{24}$ClN$_7$O$_3$ 434.1707 (M+H)$^+$. found 434.1703.

Example 9

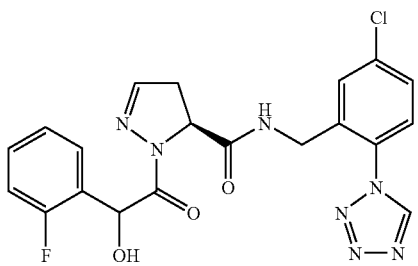

(5S)—N-[5-Chloro-2-(1H-tetrazol-1-yl)benzyl]-1-[(2-fluorophenyl)(hydroxy)acetyl]-4,5-dihydro-1H-pyrazole-5-carboxamide $^1$H NMR (500 MHz, CDCl$_3$) for the most potent isomer: δ 9.00 (s, 1H), 7.81 (br. t, 1H), 7.62 (d, 1H), 7.47 (dd, 1H), 7.35 (ddd, 1H), 7.31-7.27 (m, 2H), 7.10 (dd, 1H), 7.02 (dd, 1H), 6.91 (br. s, 1H), 5.96 (d, 1H), 4.81 (dd, 1H), 4.29 (d, 2H), 4.08 (d, 1H), 3.53 (dddd, 1H), 2.98-2.87 (m, 1H), HRMS (ESI) calculated for C$_{20}$H$_{18}$ClFN$_7$O$_3$ 458.1143 (M+H)$^+$. found 458.1136.

Example 10

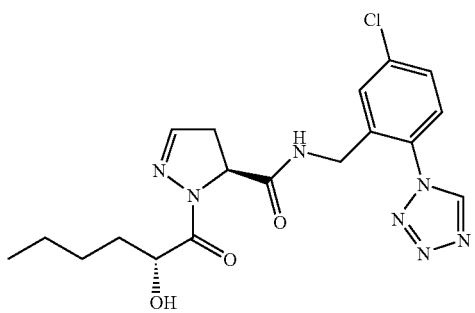

(5S)—N-[5-Chloro-2-(1H-tetrazol-1-yl)benzyl]-1-[(2R)-2-hydroxyhexanoyl]-4,5-dihydro-1H-pyrazole-5-carboxamide $^1$H NMR (600 MHz, CD$_3$CN): δ 9.19 (s, 1H), 7.69 (d, 1H), 7.54 (dd, 1H), 7.44 (d, 1H), 7.30 (br. t, 1H), 7.04 (br. t, 1H), 4.68-4.63 (m, 2H), 4.25-4.13 (m, 2H), 3.29 (d, 1H), 3.20-3.14 (dd, 1H), 2.99-2.94 (dd, 1H), 1.76-1.69 (m, 1H), 1.55-1.48 (m, 1H), 1.42-1.28 (m, 4H), 0.91 (t, 3H), HRMS (ESI) calculated for C$_{18}$H$_{22}$ClN$_7$O$_3$ 420.1551 (M+H)$^+$. found 420.1556.

Example 11

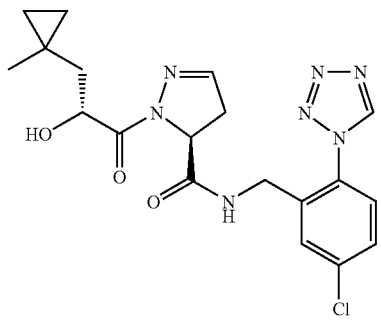

(5S)—N-[5-Chloro-2-(1H-tetrazol-1-yl)benzyl]-1-[(2R)-2-hydroxy-3-(1-methylcyclopropyl)propanoyl]-4,5-dihydro-1H-pyrazole-5-carboxamide $^1$H NMR (500 MHz, CDCl$_3$): δ 9.03 (s, 1H), 7.90 (bt, 1H), 7.61 (d, 1H), 7.47 (dd, 1H), 7.29 (d, 1H), 7.06 (s, 1H), 4.97 (ddd, 1H), 4.84 (dd, 1H), 4.28 (d, 2H), 3.61 (ddd, 1H), 3.17 (d, 1H), 3.04 (ddd, 1H), 1.70 (dd, 1H), 1.47 (dd, 1H), 1.16 (s, 3H), 0.20-0.42 (m, 4H). HRMS (ESI) calculated for C$_{19}$H$_{23}$ClN$_7$O$_3$ 432.1551 (M+H)$^+$. found 432.1541.

Example 12

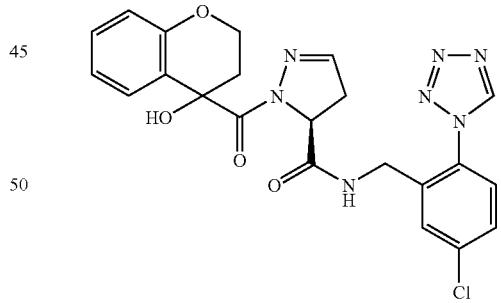

(5S)—N-[5-Chloro-2-(1H-tetrazol-1-yl)benzyl]-1-[(4-hydroxy-3,4-dihydro-2H-chromen-4-yl)carbonyl]-4,5-dihydro-1H-pyrazole-5-carboxamide $^1$H NMR (500 MHz, CDCl$_3$) for the most potent isomer: δ 8.95 (s, 1H), 7.64 (bt, 1H), 7.57 (d, 1H), 7.45 (dd, 1H), 7.26 (d, 1H), 7.13 (ddd, 1H), 6.82-6.88 (m, 2H), 6.74-6.78 (m, 2H), 4.96 (bs, 1H), 4.86 (dd, 1H), 4.18-4.38 (m, 4H), 3.36 (ddd, 1H), 2.78-2.93 (m, 2H), 1.99 (dt, 1H).

1H), 3.06 (ddd, 1H), 1.53 (dd, 1H), 1.40 (dd, 1H), 1.01 (s, 9H). HRMS (ESI) calculated for $C_{19}H_{25}ClN_7O_3$ 434.1707 (M+H)$^+$. found 434.1702.

Example 13

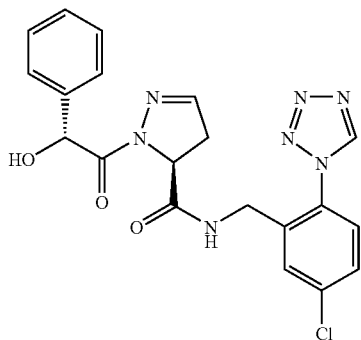

(5S)—N-[5-Chloro-2-(1H-tetrazol-1-yl)benzyl]-1-
[(2R)-2-hydroxy-2-phenylacetyl]-4,5-dihydro-1H-
pyrazole-5-carboxamide $^1$H NMR (500 MHz, CD$_3$OD): δ 9.56 (s, 1H), 7.75 (d, 1H), 7.57 (dd, 1H), 7.50 (d, 1H), 7.43-7.47 (m, 2H), 7.23-7.33 (m, 3H), 7.00 (bs, 1H), 5.88 (s, 1H), 4.59 (dd, 1H), 4.27 (q, 2H), 3.13 (ddd, 1H), 2.86 (ddd, 1H). HRMS (ESI) calculated for $C_{20}H_{19}ClN_7O_3$ 440.1238 (M+H)$^+$. found 440.1246.

Example 14

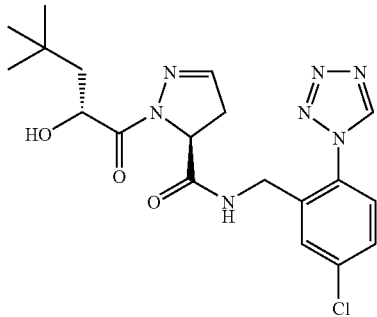

(5S)—N-[5-Chloro-2-(1H-tetrazol-1-yl)benzyl]-1-
[(2R)-2-hydroxy-4,4-dimethylpentanoyl]-4,5-dihy-
dro-1H-pyrazole-5-carboxamide $^1$H NMR (500 MHz, CDCl$_3$): δ 9.05 (s, 1H), 7.89 (bt, 1H), 7.61 (d, 1H), 7.46 (dd, 1H), 7.28 (d, 1H), 7.05 (s, 1H), 4.89 (ddd, 1H), 4.83 (dd, 1H), 4.27 (d, 2H), 3.55 (ddd, 1H), 3.16 (d,

Example 15

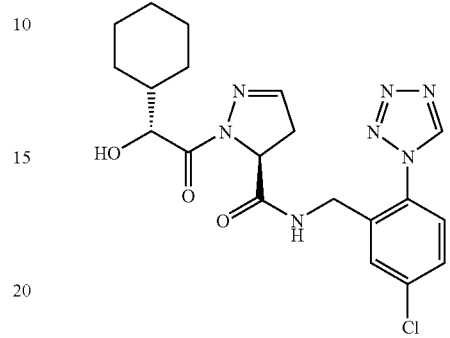

(5S)—N-[5-Chloro-2-(1H-tetrazol-1-yl)benzyl]-1-
[(2R)-2-cyclohexyl-2-hydroxyacetyl]-4,5-dihydro-
1H-pyrazole-5-carboxamide $^1$H NMR (500 MHz, CDCl$_3$): δ 9.08 (s, 1H), 7.92 (bt, 1H), 7.61 (d, 1H), 7.44 (dd, 1H), 7.28 (d, 1H), 7.05 (s, 1H), 4.85 (dd, 1H), 4.58 (d, 1H), 4.26 (d, 2H), 3.50 (ddd, 1H), 3.09 (ddd, 1H), 2.80 (bs, 1H), 1.43-1.76 (m, 6H), 1.06-1.36 (m, 5H). HRMS (ESI) calculated for $C_{20}H_{25}ClN_7O_3$ 446.1707 (M+H)$^+$. found 446.1739.

Example 16

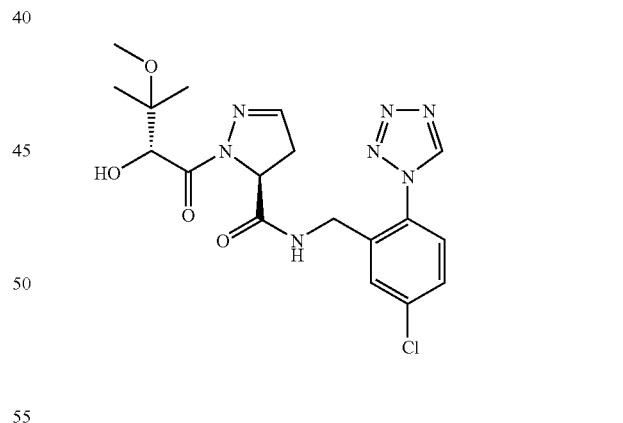

(5S)—N-[5-Chloro-2-(1H-tetrazol-1-yl)benzyl]-1-
[(2R)-2-hydroxy-3-methoxy-3-methylbutanoyl]-4,5-
dihydro-1H-pyrazole-5-carboxamide $^1$H NMR (600 MHz, CDCl$_3$): ca 3:2 mixture of diastereomers, data for major isomer: δ 9.02 (s, 1H), 7.91 (bt, 1H), 7.53 (d, 1H), 7.40 (dd, 1H), 7.25 (d, 1H), 7.01 (s, 1H), 4.75-4.93 (m, 2H), 4.10-4.25 (m, 2H), 3.17 (s, 3H), 2.95-3.60 (m, 3H), 1.19 (s, 3H), 1.17 (s, 3H).

Example 17

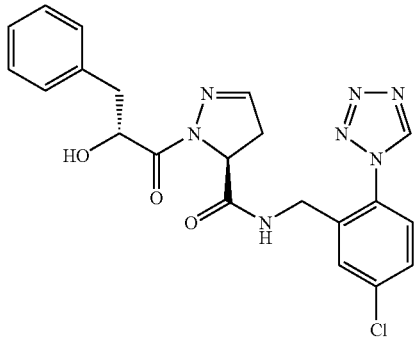

(5S)—N-[5-Chloro-2-(1H-tetrazol-1-yl)benzyl]-1-
[(2R)-2-hydroxy-3-phenylpropanoyl]-4,5-dihydro-
1H-pyrazole-5-carboxamide $^1$H NMR (500 MHz, CD$_3$OD): δ 9.54 (s, 1H), 7.73 (s, 1H), 7.55 (d, 1H), 7.48 (d, 1H), 7.15-28 (m, 5H), 7.03 (s, 1H), 5.05 (bs, 1H), 4.58-4.65 (m, 1H), 4.25 (q, 2H), 3.13-3.23 (m, 1H), 3.01-3.08 (m, 1H), 2.82-2.93 (m, 2H). HRMS (ESI) calculated for C$_{21}$H$_{21}$ClN$_7$O$_3$ 454.1394 (M+H)$^+$. found 454.1381.

Example 18

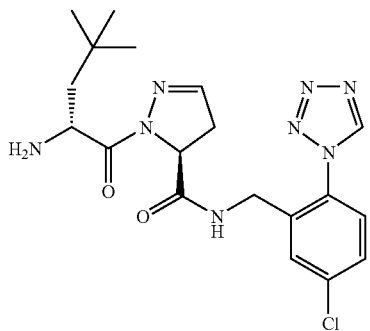

(5S)—N-[5-Chloro-2-(1H-tetrazol-1-yl)benzyl]-1-
(4-methyl-D-leucyl)-4,5-dihydro-1H-pyrazole-5-
carboxamide $^1$H NMR (500 MHz, CD$_3$OD): δ 9.54 (s, 1H), 8.90 (bs, 1H), 7.76 (s, 1H), 7.58 (d, 1H), 7.51 (d, 1H), 7.23 (s, 1H), 4.75 (bt, 1H), 4.67 (dd, 1H), 4.35 (d, 1H), 4.22 (d, 1H), 3.35 (dd, 1H), 2.96 (dd, 1H), 2.02 (dd, 1H), 1.66 (dd, 1H), 0.99 (s, 9H). HRMS (ESI) calculated for C$_{19}$H$_{26}$ClN$_8$O$_2$ 433.1867 (M+H)$^+$. found 433.1877.

Example 19

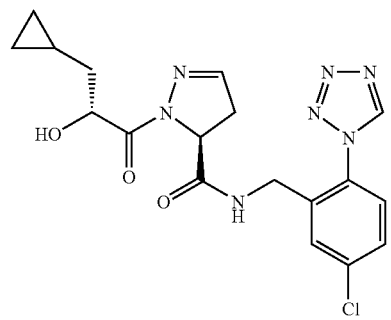

(5S)—N-[5-Chloro-2-(1H-tetrazol-1-yl)benzyl]-1-
[(2R)-3-cyclopropyl-2-hydroxypropanoyl]-4,5-dihy-
dro-1H-pyrazole-5-carboxamide $^1$H NMR (500 MHz, CD$_3$OD): δ 9.55 (s, 1H), 7.74 (s, 1H), 7.56 (d, 1H), 7.49 (d, 1H), 7.05 (s, 1H), 4.90 (bs, 1H), 4.65 (dd, 1H), 4.25 (q, 2H), 3.23 (dd, 1H), 2.90 (dd, 1H), 1.68-1.75 (m, 1H), 1.40-1.48 (m, 1H), 0.85-0.94 (m, 1H), 0.35-0.50 (m, 2H), 0.00-0.10 (m, 2H). HRMS (ESI) calculated for C$_{18}$H$_{21}$ClN$_7$O$_3$ 418.1394 (M+H)$^+$. found 418.1386.

Example 20

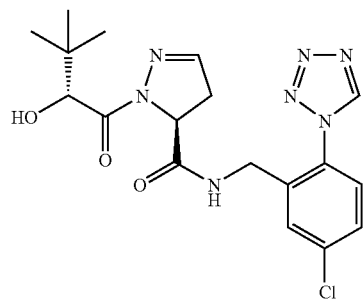

(5S)—N-[5-Chloro-2-(1H-tetrazol-1-yl)benzyl]-1-
[(2R)-2-hydroxy-3,3-dimethylbutanoyl]-4,5-dihydro-
1H-pyrazole-5-carboxamide $^1$H NMR (500 MHz, CDCl$_3$): δ 9.01 (s, 1H), 7.91 (bt, 1H), 7.58 (d, 1H), 7.43 (dd, 1H), 7.25 (d, 1H), 7.03 (s, 1H), 4.87 (dd, 1H), 4.63 (s, 1H), 4.20-4.30 (m, 2H), 3.56 (dd, 1H), 3.15 (bs, 1H), 2.99 (dd, 1H), 0.93 (s, 9H). HRMS (ESI) calculated for C$_{18}$H$_{23}$ClN$_7$O$_3$ 420.1551 (M+H)$^+$. found 420.1534.

Example 21

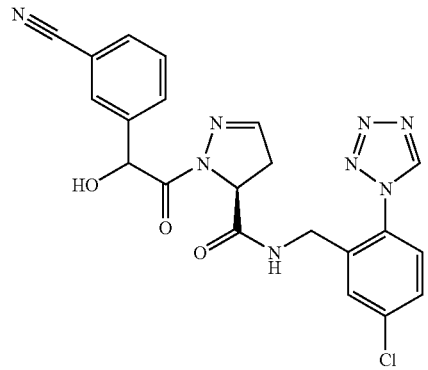

(5S)—N-[5-Chloro-2-(1H-tetrazol-1-yl)benzyl]-1-[(3-cyanophenyl)(hydroxy)acetyl]-4,5-dihydro-1H-pyrazole-5-carboxamide $^1$H NMR (400 MHz, CD$_3$CN) for the most potent isomer: δ 9.19 (s, 1H), 7.64-7.78 (m, 4H), 7.43-7.57 (m, 3H), 7.27 (bt, 1H), 7.00 (s, 1H), 5.80 (d, 1H), 4.60 (dd, 1H), 4.30 (d, 1H), 4.25 (dd, 1H), 4.16 (dd, 1H), 3.10 (ddd, 1H), 2.92 (ddd, 1H). HRMS (ESI) calculated for C$_{21}$H$_{18}$ClN$_8$O$_3$ 465.1190 (M+H)$^+$. found 465.1185.

Example 22

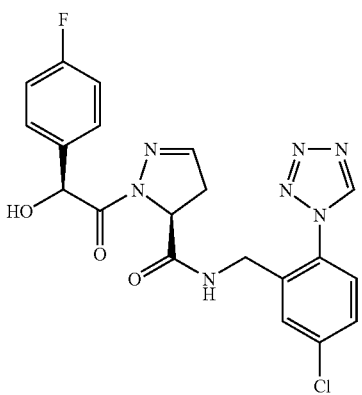

(5S)—N-[5-Chloro-2-(1H-tetrazol-1-yl)benzyl]-1-[(2S)-2-(4-fluorophenyl)-2-hydroxyacetyl]-4,5-dihydro-1H-pyrazole-5-carboxamide $^1$H NMR (500 MHz, CD$_3$CN): δ 9.19 (s, 1H), 7.67 (s, 1H), 7.57 (d, 1H), 7.48 (d, 1H), 7.40-7.45 (m, 2H), 7.21 (bt, 1H), 7.01-7.09 (m, 3H), 5.69 (d, 1H), 4.74 (dd, 1H), 4.25 (dd, 1H), 4.14 (d, 1H), 4.12 (dd, 1H), 3.19 (ddd, 1H), 2.95 (ddd, 1H). HRMS (ESI) calculated for C$_{20}$H$_{18}$ClFN$_7$O$_3$ 458.1143 (M+H)$^+$. found 458.1135.

Example 23

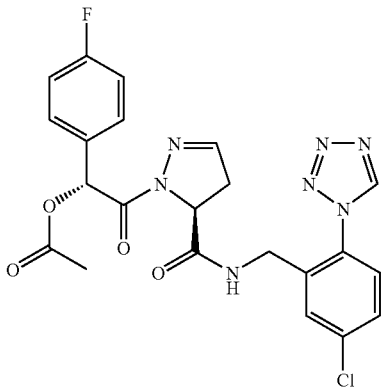

[(1R)-2-[(5S)-5-[[5-Chloro-2-(tetrazol-1-yl)phenyl]methylcarbamoyl]-4,5-dihydropyrazol-1-yl]-1-(4-fluorophenyl)-2-oxo-ethyl]acetate To (5S)—N-[5-chloro-2-(1H-tetrazol-1-yl)benzyl]-1-[(2R)-2-(4-fluorophenyl)-2-hydroxyacetyl]-4,5-dihydro-1H-pyrazole-5-carboxamide (Example 1) (483 mg, 1.05 mmol) in dichloromethane (10 mL) was added pyridine (2 mL) and acetic anhydride (100 µL, 1.06 mmol). The mixture was stirred for 4 h. Another portion of acetic anhydride (600 µL, 6.34 mmol) and DMAP (23 mg, 0.19 mmol) was added and the mixture was stirred for another 15 h. The solvents were removed by evaporation and the residue was purified by HPLC (MeCN gradient 0 to 100% in aqueous 0.1 M NH$_4$OAc buffer containing 5% MeCN, C8 column: 50×300 mm). The relevant fractions were collected, combined and freeze dried to give the title compound (476 mg, 90%) as a solid material.

$^1$H NMR (500 MHz, CDCl$_3$): δ 9.07 (s, 1H), 7.60 (d, 1H), 7.53 (m, 2H), 7.46 (dd, 1H), 7.43 (bt, 1H), 7.28 (d, 1H), 7.06 (m, 2H), 7.02 (bt, 1H), 6.53 (s, 1H), 4.81 (dd, 1H), 4.27 (dd, 1H), 4.18 (dd, 1H), 3.30 (ddd, 1H), 3.11 (ddd, 1H), 2.13 (s, 3H), HRMS (ESI) calculated for C$_{22}$H$_{19}$ClFN$_7$O$_4$ 500.1249 (M+H)$^+$. found 500.1267.

Examples 24-27 were prepared in a manner analogous to Example 23 described above using the appropriate starting materials.

Example 24

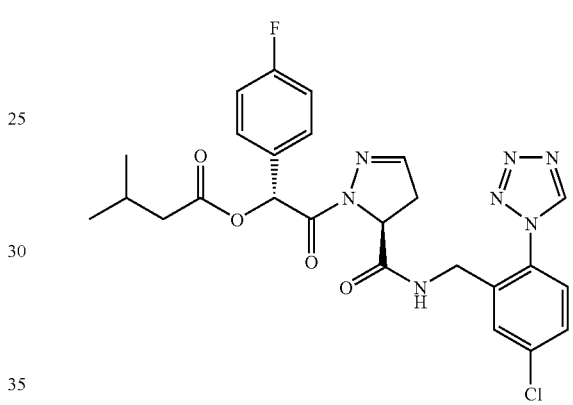

(1R)-2-[(5S)-5-{[5-Chloro-2-(1H-tetrazol-1-yl)benzyl]carbamoyl}-4,5-dihydro-1H-pyrazol-1-yl]-1-(4-fluorophenyl)-2-oxoethyl 3-methylbutanoate $^1$H NMR (500 MHz, (CH$_3$)$_2$SO*): δ 9.79 (s, 1H), 8.76 (t, 1H), 7.66 (1H), 7.60 (m, 2H), 7.45 (m, 2H), 7.19 (t, 2H), 7.15 (s, 1H), 6.59 (s, 1H), 4.54 (dd, 1H), 4.20 (dd, 1H), 4.04 (dd, 1H), 3.13 (dd, 1H), 2.73 (dd, 1H), 2.20 (m, 1H), 1.92, (m, 1H), 0.84 (dd, 6H), HRMS (ESI) calculated for C$_{25}$H$_{25}$ClFN$_7$O$_4$ (M+H)$^+$, 542.1719 found 542.1715.

Example 25

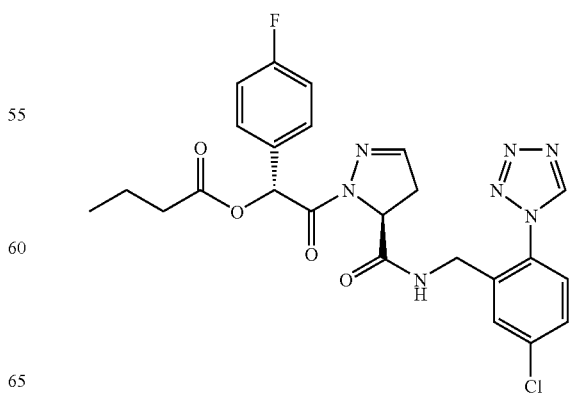

(1R)-2-[(5S)-5-{[5-Chloro-2-(1H-tetrazol-1-yl)benzyl]carbamoyl}-4,5-dihydro-1H-pyrazol-1-yl]-1-(4-fluorophenyl)-2-oxoethyl butanoate ¹H NMR (500 MHz, (CH₃)₂SO*): δ 9.80 (s, 1H), 8.49 (t, 1H), 7.67 (1H), 7.60 (m, 2H), 7.45 (m, 2H), 7.18 (t, 2H), 7.15 (s, 1H), 6.59 (s, 1H), 4.54 (dd, 1H), 4.20 (dd, 1H), 4.05 (dd, 1H), 3.14 (dd, 1H), 2.31 (m, 2H), 1.50, (m, 2H), 0.83 (t, 3H),
HRMS (ESI) calculated for $C_{24}H_{23}ClFN_7O_4$ (M+H)⁺, 528.1563 found 528.1573.

Example 26

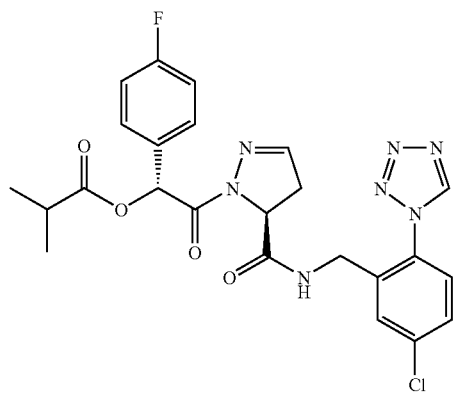

(1R)-2-[(5S)-5-{[5-Chloro-2-(1H-tetrazol-1-yl)benzyl]carbamoyl}-4,5-dihydro-1H-pyrazol-1-yl]-1-(4-fluorophenyl)-2-oxoethyl 2-methylpropanoate ¹H NMR (500 MHz, (CH₃)₂SO*): δ 9.79 (s, 1H), 8.47 (t, 1H), 7.67 (1H), 7.60 (m, 2H), 7.45 (m, 2H), 7.19 (t, 2H), 7.15 (s, 1H), 6.58 (s, 1H), 4.54 (dd, 1H), 4.21 (dd, 1H), 4.05 (dd, 1H), 3.15 (dd, 1H), 2.57 (m, 1H), 1.07 (d, 3H), 1.03 (d, 3H),
HRMS (ESI) calculated for $C_{24}H_{23}ClFN_7O_4$ (M+H)⁺, 528.1563 found 528.1569.

Example 27

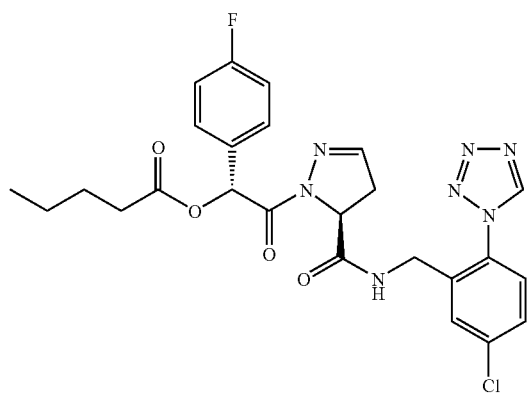

(1R)-2-[(5S)-5-{[5-Chloro-2-(1H-tetrazol-1-yl)benzyl]carbamoyl}-4,5-dihydro-1H-pyrazol-1-yl]-1-(4-fluorophenyl)-2-oxoethyl pentanoate ¹H NMR (500 MHz, (CH₃)₂SO*): δ 9.80 (s, 1H), 8.49 (t, 1H), 7.67 (1H), 7.60 (m, 2H), 7.45 (m, 2H), 7.19 (t, 2H), 7.15 (s, 1H), 6.58 (s, 1H), 4.54 (dd, 1H), 4.20 (dd, 1H), 4.05 (dd, 1H), 3.14 (dd, 1H), 2.73 (dd, 1H), 2.33 (m, 2H), 1.45, (m, 2H), 1.24 (m, 2H), 0.80 (t, 3H),
HRMS (ESI) calculated for $C_{25}H_{25}ClFN_7O_4$ (M+H)⁺, 542.1719 found 542.1719.

Example 28

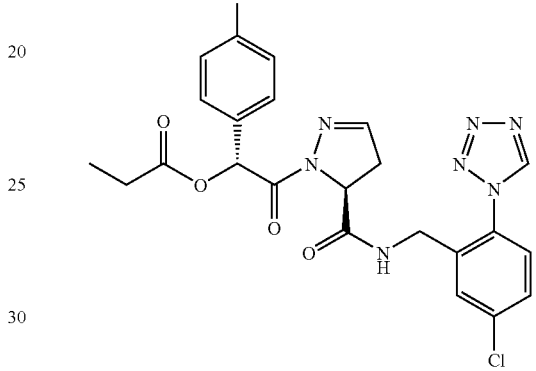

(1R)-2-[(5S)-5-{[5-Chloro-2-(1H-tetrazol-1-yl)benzyl]carbamoyl}-4,5-dihydro-1H-pyrazol-1-yl]-1-(4-fluorophenyl)-2-oxoethyl propanoate To a suspension of (5S)—N-[5-chloro-2-(1H-tetrazol-1-yl)benzyl]-1-[(2R)-2-(4-fluorophenyl)-2-hydroxyacetyl]-4,5-dihydro-1H-pyrazole-5-carboxamide (Example 1) (276 g, 603 mmol) in 2-methyl THF (4.6 L) was added pyridine (62 mL) followed by N,N-dimethylpyridine-4-amine (7.36 g, 723 mmol) and propionic anhydride (93 mL, 723 mmol). After 2 h the suspension became a little bit thicker and after 3 h the suspension was very thick. Another portion of 2-methyl THF (2 L) was added and an extra impeller was assembled to the stirring bar. The suspension was stirred at 30° C. (jacket temp) over night. The temperature was then lowered to 15° C. and after 30 minutes the reaction mixture was filtered through a P3 sintered glass funnel and the filter cake was washed with ethylacetate (2×250 mL). The white product was dried at 40° C. in vacuo to give the title compound (238 g, 77%) as a solid material. To the mother liquor (7.6 L) water (2 L) was added and the phases were separated. The organic phase was evaporated gently until a thick precipitation was observed. The slurry was filtered off to get, after drying, a second crop of the title compound (37 g, 12%).

¹H NMR (500 MHz, (CDCl₃): δ 9.05 (s, 1H), 7.55 (m, 3H), 7.43 (m, 2H), 7.25 (s, 1H), 7.04 (m, 3H), 6.52 (s, 1H), 4.79 (dd, 1H), 4.22 (dd, 2H), 3.25 (ddd, 1H), 3.09 (ddd, 1H), 2.41 (m, 2H), 1.03 (t, 3H).
HRMS (ESI) calculated for $C_{23}H_{21}ClFN_7O_4$ (M+H)⁺, 514.1406 found 514.1405.

Example 29

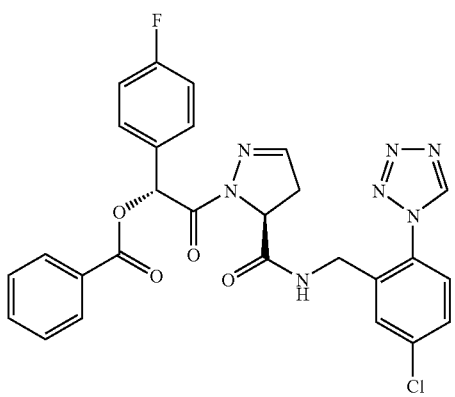

(1R)-2-[(5S)-5-{[5-Chloro-2-(1H-tetrazol-1-yl)ben-zyl]carbamoyl}-4,5-dihydro-1H-pyrazol-1-yl]-1-(4-fluorophenyl)-2-oxoethyl benzoate To a mixture of (3S)—N—[[5-chloro-2-(tetrazol-1-yl)phenyl]methyl]-2-[(2R)-2-(4-fluorophenyl)-2-hydroxy-acetyl]-3,4-dihydropyrazole-3-carboxamide (0.48 g, 1.05 mmol), pyridine (6 mL, 74 mmol), and DMAP (0.023 g, 0.188 mmol) in CH$_2$Cl$_2$ (8 mL) at −10° C. was added benzoyl chloride (135 µL, 1.15 mmol). The reaction mixture was allowed to attain rt and was stirred for 5 h. Another portion of benzoyl chloride (400 µL, 3.4 mmol) was added. The mixture was stirred for 60 h. LCMS analysis indicated only a trace amount of product. The solvents were removed by evaporation and pyridine (5 mL, 62 mmol) was added followed by another portion of benzoyl chloride (400 µL, 3.4 mmol). The reaction mixture was heated to 70° C. overnight. LCMS analysis indicated approximately 20% conversion of starting material. The solvent was evaporated of and the residue was purified by HPLC (MeCN gradient 0 to 100% in 0.1 M NH$_4$OAc buffer containing 5% MeCN). The relevant fractions were combined and lyophilized to give the title compound (77 mg, 13%) together with 289 mg of unreacted starting material.

$^1$H NMR (500 MHz, CDCl$_3$): δ 9.07 (s, 1H), 7.86 (d, 2H), 7.64 (m, 2H), 7.59 (m, 1H), 7.55 (d, 1H), 7.50 (bt, 1H), 7.42 (t, 2H), 7.36 (dd, 1H), 7.23 (d, 1H), 7.12-7.05 (m, 3H), 6.77 (s, 1H), 4.81 (dd, 1H), 4.28 (ddd, 2H), 3.27 (ddd, 1H), 3.13 (ddd, 1H), HRMS (ESI) calculated for C$_{27}$H$_{21}$ClFN$_7$O$_4$ 562.1406 (M+H)$^+$. found 562.1390.

Example 30

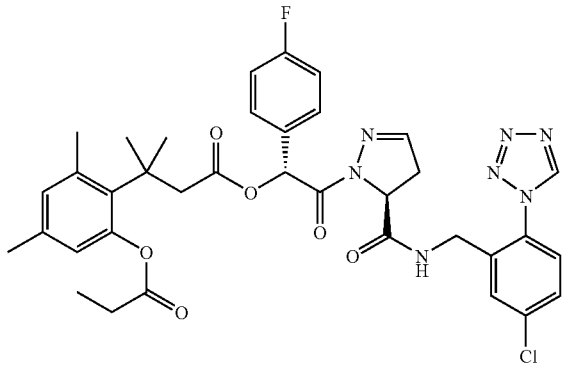

(R)-2-((S)-5-(5-Chloro-2-(1H-tetrazol-1-yl)benzyl-carbamoyl)-4,5-dihydro-1H-pyrazol-1-yl)-1-(4-fluorophenyl)-2-oxoethyl 3-(2,4-dimethyl-6-(propionyloxy)phenyl)-3-methylbutanoate To a solution of 3-(2,4-dimethyl-6-(propionyloxy)phenyl)-3-methylbutanoic acid (160 mg, 0.57 mmol) and (S)—N-(5-chloro-2-(1H-tetrazol-1-yl)benzyl)-1-((R)-2-(4-fluorophenyl)-2-hydroxyacetyl)-4,5-dihydro-1H-pyrazole-5-carboxamide (263 mg, 0.57 mmol) in DCM (3 mL) and DMF (3 mL) was added EDC (165 mg, 0.86 mmol) and DMAP (7 mg, 0.06 mmol). The clear colorless solution was stirred at rt for 48 h. The mixture was diluted with DCM and washed with water, 1M HCl and sat NaHCO$_3$. The organic phase was dried, filtered, evaporated and purified by flash chromatography (DCM/EtOAc gradient from 4:1 to 2:1) to give (R)-2-((S)-5-(5-chloro-2-(1H-tetrazol-1-yl)benzylcarbamoyl)-4,5-dihydro-1H-pyrazol-1-yl)-1-(4-fluorophenyl)-2-oxoethyl 3-(2,4-dimethyl-6-(propionyloxy)phenyl)-3-methylbutanoate (380 mg, 92%) as a semisolid.

$^1$H NMR (500 MHz, CDCl$_3$): δ 9.08 (s, 1H), 7.33-7.48 (m, 5H), 7.22-7.26 (m, 1H), 6.95-7.03 (m, 3H), 6.70 (s, 1H), 6.48 (s, 1H), 6.40 (s, 1H), 4.77 (dd, 1H), 4.03 (dd, 1H), 3.96 (dd, 1H), 3.21 (ddd, 1H), 2.90-3.10 (m, 3H), 2.52 (q, 2H), 2.48 (s, 3H), 2.11 (s, 3H), 1.54 (s, 3H), 1.46 (s, 3H), 1.19 (t, 3H). HRMS (ESI) calculated for C$_{36}$H$_{37}$ClFN$_7$O$_6$ 718.17 (M+H)$^+$. found 718.2556 (M+H)$^+$. found 718.2578.

Example 31

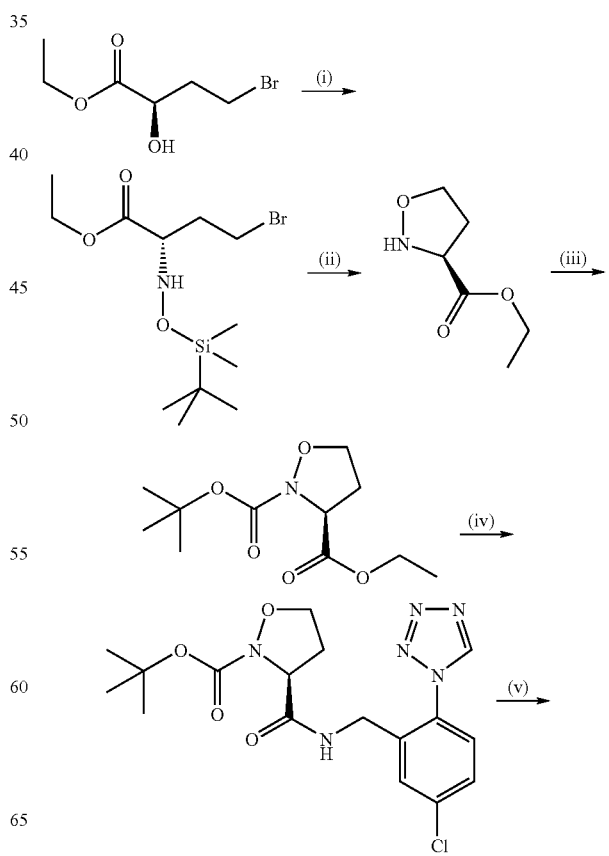

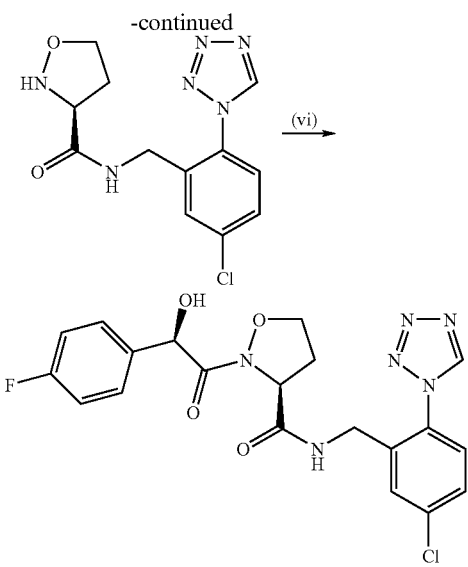

(3S)—N-[5-Chloro-2-(1H-tetrazol-1-yl)benzyl]-2-[(2R)-2-(4-fluorophenyl)-2-hydroxyacetyl]isoxazolidine-3-carboxamide (i) Ethyl (2S)-4-bromo-2-({[tert-butyl(dimethyl)silyl]oxy}amino)butanoate To a solution of (R)-4-bromo-2-hydroxy-butyric acid ethyl ester (890 mg, 4.217 mmol) in DCM (20 mL) was added trifluoromethanesulfonic anhydride (1.309 g, 4.639 mmol) dropwise at 0° C. After 5 min, 2,6-dimethylpyridine (542 mg, 5.060 mmol) was added and the mixture was allowed to attain rt. After 30 min, O-(tert-butyldimethylsilyl)hydroxylamine (932 mg, 6.326 mmol) and 2,6-dimethylpyridine (1.808 g, 16.87 mmol) was added and the reaction mixture was stirred at rt for 48 h. The solvents were evaporated and the residue was purified by flash chromatography (heptane/EtOAc 20:1, then 9:1) to give (S)-4-bromo-2-N-(tert-butyldimethylsilyl)hydroxylamino-butyric acid ethyl ester (870 mg, 61%) as an oil.

(ii) Ethyl (3S)-isoxazolidine-3-carboxylate

To a solution of ethyl (2S)-4-bromo-2-({[tert-butyl(dimethyl)silyl]oxy}amino)butanoate (870 mg, 2.556 mmol) in THF (25 mL) was added tetrabutylammoniumfluoride trihydrate (887 mg, 2.812 mmol) and the mixture was stirred at rt for 1 h. The solvents were evaporated and the residue was purified by flash chromatography (DCM/EtOAc 9:1, then 4:1) to give ethyl (3S)-isoxazolidine-3-carboxylate (340 mg, 91%) as an oil.

(iii) 2-tert-Butyl 3-ethyl (3S)-isoxazolidine-2,3-dicarboxylate

To a solution of ethyl (3S)-isoxazolidine-3-carboxylate (1.452 g, 10.00 mmol) in DCM (20 mL) was added boc-anhydride (2.62 g, 12.00 mmol), triethylamine (2.02 g, 20.00 mmol) and dimethylaminopyridine (61 mg, 0.500 mmol). The reaction mixture was stirred at rt over night and was then diluted with TBME and washed with 1 M HCl followed by saturated NaHCO$_3$(aq). The organic phase was dried, filtered, evaporated and the residue was purified by flash chromatography (heptane/EtOAc 4:1, then 2:1) to give 2-tert-butyl 3-ethyl (3S)-isoxazolidine-2,3-dicarboxylate (2.20 g, 90%) as an oil.

(iv) tert-Butyl (3S)-3-{[5-chloro-2-(1H-tetrazol-1-yl)benzyl]carbamoyl}isoxazolidine-2-carboxylate To a solution of 2-tert-butyl 3-ethyl (3S)-isoxazolidine-2,3-dicarboxylate (245 mg, 1.00 mmol) in acetonitrile (2.5 mL) and water (1 mL) was added lithium hydroxide (1 M in water, 1.00 mL, 1.00 mmol) and the mixture was stirred at rt for 30 min. To this solution was added 5-chloro-2-tetrazol-1-yl-benzylamine hydrochloride (295 mg, 1.20 mmol, prepared as described in *J. Med. Chem.* 2004, 47, 2995), hydroxybenzotriazole (135 mg, 1.00 mmol, as a 20% solution in water, ca 0.65 mL), EDC (288 mg, 1.50 mmol) and NMM (202 mg, 2.00 mmol). The resulting mixture was stirred at rt over night, then diluted with DCM and washed with 1 M HCl and saturated sodium hydrogen carbonate. The organic phase was dried, filtered, evaporated and purified by flash chromatography (DCM/EtOAc gradient from 4:1 to 1:1) to give tert-butyl (3S)-3-{[5-chloro-2-(1H-tetrazol-1-yl)benzyl]carbamoyl}isoxazolidine-2-carboxylate (357 mg, 87%) as an oil.

(v) (3S)—N-[5-Chloro-2-(1H-tetrazol-1-yl)benzyl]isoxazolidine-3-carboxamide hydrochloride To a solution of tert-butyl (3S)-3-{[5-chloro-2-(1H-tetrazol-1-yl)benzyl]carbamoyl}isoxazolidine-2-carboxylate (357 mg, 0.873 mmol) in MeOH (5 mL) was added conc. HCl (aq., 5 mL) and the mixture was stirred at rt for 1 h and then evaporated to dryness to give crude (3S)—N-[5-chloro-2-(1H-tetrazol-1-yl)benzyl]isoxazolidine-3-carboxamide hydrochloride as a solid which was used as such in the next reaction without further purification.

(vi) (3S)—N-[5-Chloro-2-(1H-tetrazol-1-yl)benzyl]-2-[(2R)-2-(4-fluorophenyl)-2-hydroxyacetyl]isoxazolidine-3-carboxamide To a solution containing dichloromethane (150 mL) and pyridine (11 mL) was added (3S)—N-[5-chloro-2-(1H-tetrazol-1-yl)benzyl]isoxazolidine-3-carboxamide hydrochloride (8.40 g, 27.21 mmol) followed by the crude solution of the (R)-2-(4-fluorophenyl)-2-(trimethylsilyloxy)acetyl chloride (7.80 g, 29.93 mmol, see Preparation 2) in dichloromethane (~0.3 M, 100 mL). The resulting solution was stirred at room temperature for 12 h. MeOH (10 mL) was added and the reaction mixture was stirred for another 1 h. The mixture was diluted with dichloromethane (200 mL), washed with 1 M HCl (3×200 mL), sat NaHCO$_3$ (100 mL) and brine (100 mL), dried, filtered and evaporated to give the crude product. CH$_2$Cl$_2$/EtOAc (50 mL, 1:1) was added and the mixture was heated to reflux. A solution was obtained. Toluene/EtOAc (1:1, 50 mL) was then added dropwise resulting in some precipitation. After 12 h the precipitate (6.1 g) was filtered of. $^1$HNMR analysis indicated pure product. The mother liquor was evaporated. To the residue was added CH$_2$Cl$_2$/EtOAc (30 mL, 1:1) and the mixture was heated to reflux. A solution was obtained. Toluene/EtOAc (1:1, 30 mL) was added dropwise. After another 12 h, another 500 mg of precipitate could be filtered off (this material was pure according to $^1$HNMR). Total yield of (3S)—N-[5-chloro-2-(1H-tetrazol-1-yl)benzyl]-2-[(2R)-2-(4-fluorophenyl)-2-hydroxyacetyl]isoxazolidine-3-carboxamide (6.6 g, 53%).

¹H NMR (600 MHz, CDCl₃) for the most potent isomer: δ 2.25-2.33 (1H), 2.58-2.67 (1H), 2.75-2.82 (1H), 3.84-3.89 (1H), 4.11-4.15 (1H), 4.24-4.34 (2H), 4.60-4.65 (1H), 5.47-5.51 (1H), 7.01-7.06 (2H), 7.26-7.30 (1H), 7.31-7.36 (3H), 7.45-7.48 (1H), 7.60-7.62 (1H), 8.97 (1H). HRMS (ES⁺) calculated for $C_{20}H_{18}ClFN_6O_4$ 461.1140 (M+H)⁺. found 461.1122.

Examples 32-48 were prepared in a manner analogous to Example 31 described above using the appropriate starting materials.

Example 32

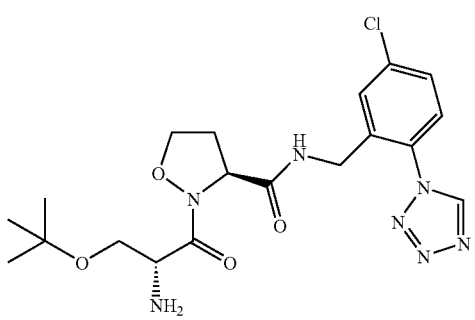

(3S)-2-(O-tert-Butyl-D-seryl)-N-[5-chloro-2-(1H-tetrazol-1-yl)benzyl]isoxazolidine-3-carboxamide ¹H NMR (500 MHz, CDCl₃): δ 8.99 (s, 1H), 8.00 (br. s, 1H), 7.64 (d, 1H), 7.44 (dd, 1H), 7.26 (m, 1H), 6.99 (br. t, 1H), 5.41 (br. s, 1H), 4.44 (m, 1H), 4.27-4.02 (m, 4H), 3.89 (dd, 1H), 3.63 (dd, 1H), 3.43 (dd, 1H), 2.70 (m, 1H), 2.50 (m, 1H), 1.17 (s, 9H), HRMS (ESI) calculated for $C_{19}H_{27}ClN_7O_4$ 452.1813 (M+H)⁺. found 452.1821.

Example 33

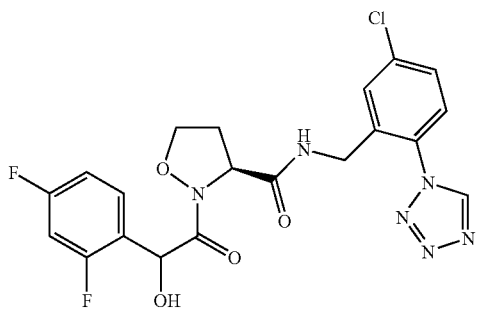

(3S)—N-[5-Chloro-2-(1H-tetrazol-1-yl)benzyl]-2-[(2,4-difluorophenyl)(hydroxy)acetyl]isoxazolidine-3-carboxamide ¹H NMR (500 MHz, CDCl₃) for the most potent isomer: δ 2.32-2.41 (1H), 2.62-2.72 (1H), 2.85-2.93 (1H), 3.89-3.96 (1H), 4.20 (1H), 4.26-4.37 (2H), 4.66-4.73 (1H), 5.74 (1H), 6.81-6.95 (2H), 7.26-7.34 (2H), 7.37-7.44 (1H), 7.46-7.52 (1H), 7.61-7.66 (1H), 9.01 (1H). HRMS (ES+) calculated for $C_{20}H_{17}ClF_2N_6O_4$ 479.1046 (M+H)⁺. found 479.1059.

Example 34

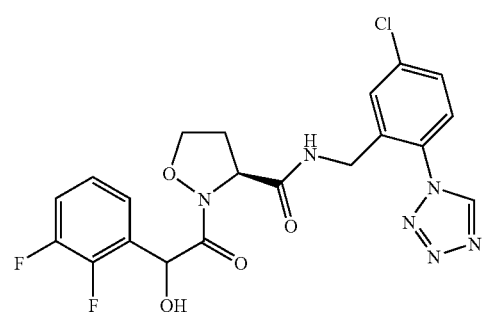

(3S)—N-[5-Chloro-2-(1H-tetrazol-1-yl)benzyl]-2-[(2,3-difluorophenyl)(hydroxy)acetyl]isoxazolidine-3-carboxamide ¹H NMR (400 MHz, CDCl₃): δ 8.97 (s, 1H), 7.62 (d, 1H), 7.47 (dd, 1H), 7.33 (br. t, 1H), 7.29 (d, 1H), 7.18-7.03 (m, 3H), 5.78 (s, 1H), 4.67 (dd, 1H), 4.36-4.24 (m, 2H), 4.16 (br., 1H), 3.94-3.88 (m, 1H), 2.91-2.83 (m, 1H), 2.73-2.62 (m, 1H), 2.40-2.30 (m, 1H), HRMS (ESI) calculated for $C_{20}H_{17}ClF_2N_6O_4$ 479.1046 (M+H)⁺. found 479.1053.

Example 35

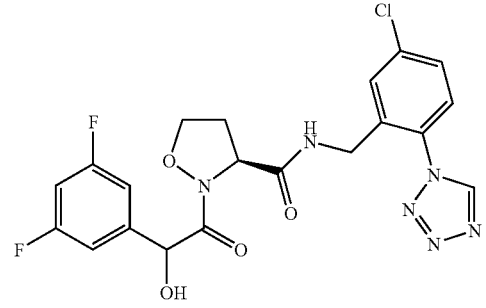

(3S)—N-[5-Chloro-2-(1H-tetrazol-1-yl)benzyl]-2-[(3,5-difluorophenyl)(hydroxy)acetyl]isoxazolidine-3-carboxamide ¹H NMR (400 MHz, CDCl₃) for the most potent isomer: δ 8.96 (s, 1H), 7.62 (d, 1H), 7.48 (dd, 1H), 7.31 (br. t, 1H), 7.28 (d, 1H), 6.96-6.89 (m, 2H), 6.81-6.73 (m, 1H), 5.49 (d, 1H), 4.64 (dd, 1H), 4.36-4.25 (m, 2H), 4.21 (d, 1H), 4.03-3.97 (m, 1H), 3.14-3.05 (m, 1H), 2.76-2.66 (m, 1H), 2.42-2.32 (m, 1H), HRMS (ESI) calculated for $C_{20}H_{17}ClF_2N_6O_4$ 479.1046 (M+H)⁺. found 479.1030.

Example 36

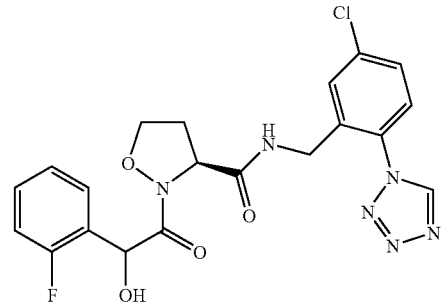

(3S)—N-[5-Chloro-2-(1H-tetrazol-1-yl)benzyl]-2-[(2-fluorophenyl)(hydroxy)acetyl]isoxazolidine-3-carboxamide ¹H NMR (600 MHz, CDCl₃): δ 2.27-2.35 (1H), 2.60-2.68 (1H), 2.70-2.77 (1H), 3.81-3.87 (1H), 4.24-4.34 (2H), 4.65-4.70 (1H), 5.76 (1H), 7.04-7.10 (1H), 7.11-7.16 (1H), 7.26-7.34 (4H), 7.45-7.50 (1H), 7.59-7.62 (1H), 8.96 (1H). HRMS (ES+) calculated for $C_{20}H_{18}ClFN_6O_4$ 461.1140 (M+H)⁺. found 461.1151.

Example 37

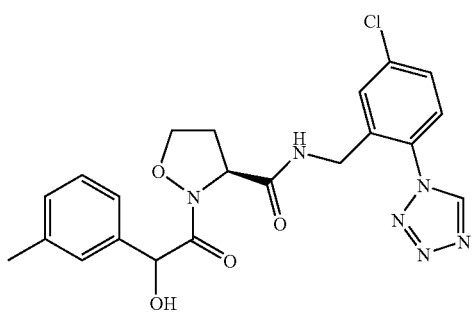

(3S)—N-[5-Chloro-2-(1H-tetrazol-1-yl)benzyl]-2-[hydroxy(3-methylphenyl)acetyl]isoxazolidine-3-carboxamide ¹H NMR (500 MHz, CDCl₃) for the most potent isomer: δ 9.02 (s, 1H), 7.60 (d, 1H), 7.47 (br. t, 1H), 7.44 (dd, 1H), 7.24-7.09 (m, 5H), 5.45 (d, 1H), 4.64 (dd, 1H), 4.34-4.21 (m, 2H), 4.14 (d, 1H), 3.85-3.78 (m, 1H), 2.76-2.67 (m, 1H), 2.62-2.51 (m, 1H), 2.32 (s, 3H), 2.32-2.22 (m, 1H), HRMS (ESI) calculated for $C_{21}H_{21}ClN_6O_4$ 457.1391 (M+H)⁺. found 457.1390.

Example 38

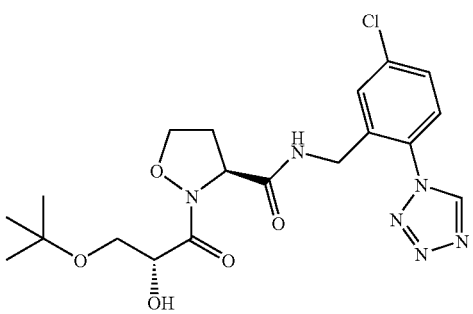

(3S)—N-[5-Chloro-2-(1H-tetrazol-1-yl)benzyl]-2-[(2R)-2-hydroxyhexanoyl]isoxazolidine-3-carboxamide ¹H NMR (600 MHz, CDCl₃): δ 0.86-0.92 (3H), 1.23-1.54 (5H), 1.58-1.66 (1H), 2.47-2.55 (1H), 2.77-2.84 (1H), 3.22 (1H), 3.85-3.91 (1H), 4.16-4.22 (1H), 4.22-4.31 (2H), 4.47-4.52 (1H), 4.69-4.74 (1H), 7.24-7.26 (1H), 7.42-7.45 (1H), 7.50-7.56 (1H), 7.57-7.60 (1H), 9.00 (1H). HRMS (ES+) calculated for $C_{18}H_{23}ClN_6O_4$ 423.1548 (M+H)⁺. found 423.1535.

Example 39

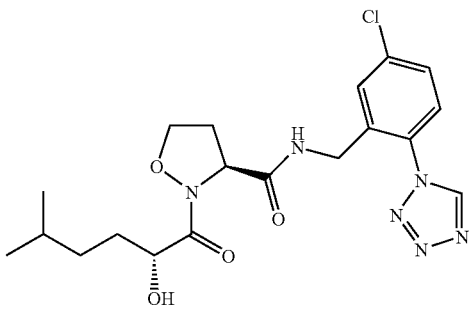

(3S)—N-[5-Chloro-2-(1H-tetrazol-1-yl)benzyl]-2-[(2R)-2-hydroxy-5-methylhexanoyl]isoxazolidine-3-carboxamide ¹H NMR (600 MHz, CDCl₃): δ 0.84-0.92 (6H), 1.24-1.40 (2H), 1.47-1.69 (3H), 2.46-2.55 (1H), 2.81-2.89 (1H), 3.11 (1H), 3.86-3.93 (1H), 4.17-4.33 (3H), 4.48-4.53 (1H), 4.69-4.75 (1H), 7.26-7.28 (1H), 7.42-7.48 (2H), 7.57-7.60 (1H), 8.96 (1H). HRMS (ES+) calculated for $C_{19}H_{25}ClN_6O_4$ 437.1704 (M+H)⁺. found 437.1715.

Example 40

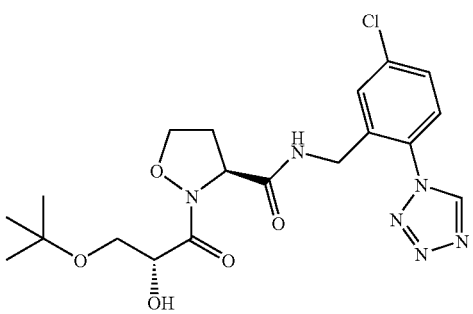

(3S)-2-[(2R)-3-tert-Butoxy-2-hydroxypropanoyl]-N-[5-chloro-2-(1H-tetrazol-1-yl)benzyl]isoxazolidine-3-carboxamide ¹H NMR (600 MHz, CDCl₃): δ 1.14 (9H), 2.45-2.54 (1H), 2.74-2.83 (1H), 3.51-3.57 (1H), 3.64-3.69 (1H), 3.92-3.99 (1H), 4.13-4.19 (1H), 4.21-4.31 (2H), 4.65-4.70 (1H), 4.73-4.79 (1H), 7.24-7.28 (1H), 7.42-7.46 (1H), 7.48-7.54 (1H), 7.56-7.60 (1H), 9.00 (1H). HRMS (ES+) calculated for $C_{19}H_{25}ClN_6O_5$ 453.1653 (M+H)⁺. found 423.1571.

Example 41

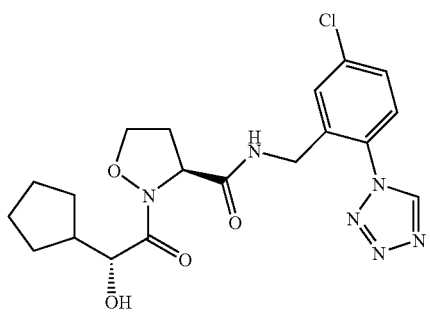

(3S)—N-[5-Chloro-2-(1H-tetrazol-1-yl)benzyl]-2-
[(2R)-2-cyclopentyl-2-hydroxyacetyl]isoxazolidine-
3-carboxamide $^1$H NMR (600 MHz, CDCl$_3$): δ 1.40-1.72 (8H), 2.12-2.20 (1H), 2.46-2.55 (1H), 2.80-2.90 (1H), 3.87-3.94 (1H), 4.16-4.31 (3H), 4.49-4.52 (1H), 4.70-4.75 (1H), 7.26-7.28 (1H), 7.43-7.47 (1H), 7.52-7.60 (2H), 8.99 (1H). HRMS (ES+) calculated for C$_{19}$H$_{23}$ClN$_6$O$_4$ 435.1548 (M+H)$^+$. found 435.1559.

Example 42

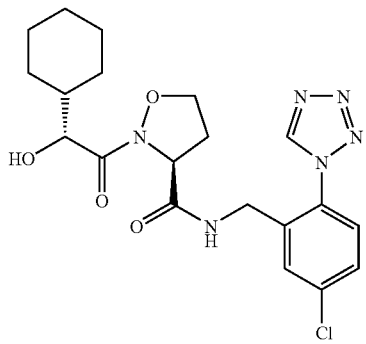

(3S)—N-[5-Chloro-2-(1H-tetrazol-1-yl)benzyl]-2-
[(2R)-2-cyclohexyl-2-hydroxyacetyl]isoxazolidine-
3-carboxamide $^1$H NMR (500 MHz, CDCl$_3$): δ 8.99 (s, 1H), 7.59 (d, 1H), 7.57 (br. t, 1H), 7.45 (dd, 1H), 7.27 (m, 1H), 4.73 (dd, 1H), 4.37 (d, 1H), 4.27 (m, 2H), 4.20 (m, 1H), 3.89 (q, 1H), 2.85 (m, 1H), 2.51 (m, 1H), 1.82-1.70 (m, 2H), 1.69-1.53 (m, 3H), 1.52-1.42 (m, 1H), 1.41-1.30 (m, 1H), 1.29-1.07 (m, 4H). HRMS (ESI) calculated for C$_{20}$H$_{26}$ClN$_6$O$_4$ 449.1704 (M+H)$^+$. found 449.1725.

Example 43

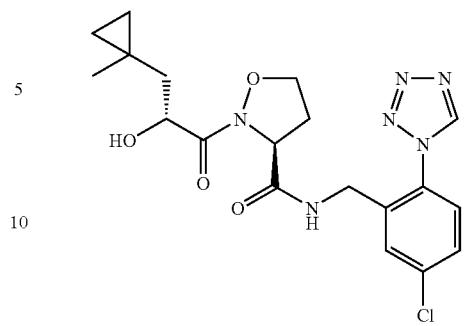

(3S)—N-[5-Chloro-2-(1H-tetrazol-1-yl)benzyl]-2-
[(2R)-2-hydroxy-3-(1-methylcyclopropyl)propanoyl]
isoxazolidine-3-carboxamide $^1$H NMR (500 MHz, CDCl$_3$): δ 9.02 (s, 1H), 7.60 (d, 1H), 7.57 (bt. 1H), 7.44 (dd, 1H), 7.26 (d, 1H), 4.66-4.72 (m, 2H), 4.23-4.33 (m, 2H), 4.18 (ddd, 1H), 3.92 (q, 1H), 3.17 (d, 1H), 2.77-2.85 (m, 1H), 2.46-2.54 (m, 1H), 1.60 (dd, 1H), 1.38 (dd, 1H), 1.13 (s, 3H), 0.21-0.45 (m, 4H). HRMS (ESI) calculated for C$_{19}$H$_{24}$ClN$_6$O$_4$ 435.1548 (M+H)$^+$. found 435.1535.

Example 44

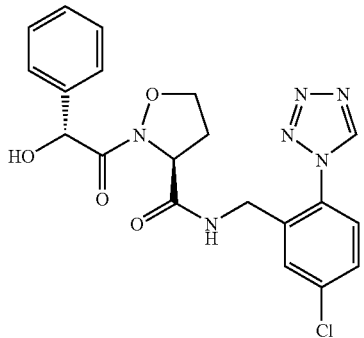

(3S)—N-[5-Chloro-2-(1H-tetrazol-1-yl)benzyl]-2-
[(2R)-2-hydroxy-2-phenylacetyl]isoxazolidine-3-
carboxamide $^1$H NMR (400 MHz, CDCl$_3$): δ 9.02 (s, 1H), 7.61 (d, 1H), 7.47 (bt, 1H), 7.44 (dd, 1H), 7.12-7.35 (m, 6H), 5.49 (d, 1H), 4.64 (dd, 1H), 4.22-4.33 (m, 2H), 4.20 (d, 1H), 3.81 (ddd, 1H), 2.64-2.72 (m, 1H), 2.52-2.62 (m, 1H), 2.22-2.31 (m, 1H). HRMS (ESI) calculated for C$_{20}$H$_{20}$ClN$_6$O$_4$ 443.1234 (M+H)$^+$. found 443.1234.

Example 45

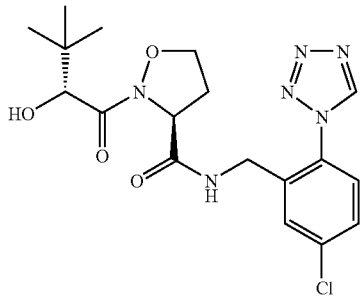

(3S)—N-[5-Chloro-2-(1H-tetrazol-1-yl)benzyl]-2-[(2R)-2-hydroxy-3,3-dimethylbutanoyl]isoxazolidine-3-carboxamide ¹H NMR (500 MHz, CDCl₃): δ 9.04 (s, 1H), 7.73 (bt, 1H), 7.58 (d, 1H), 7.42 (dd, 1H), 7.25 (d, 1H), 4.75 (dd, 1H), 4.22-4.30 (m, 3H), 4.11-4.17 (ddd, 1H), 3.97 (q, 1H), 3.12 (bs, 1H), 2.77-2.88 (m, 1H), 2.40-2.50 (m, 1H), 0.94 (s, 9H). HRMS (ESI) calculated for $C_{18}H_{24}ClN_6O_4$ 423.1548 (M+H)⁺. found 423.1552.

Example 46

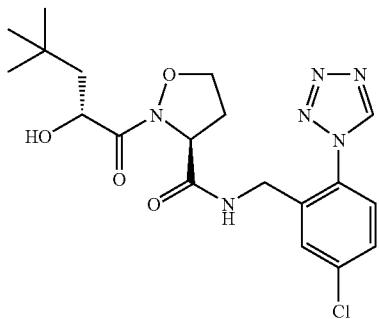

(3S)—N-[5-Chloro-2-(1H-tetrazol-1-yl)benzyl]-2-[(2R)-2-hydroxy-4,4-dimethylpentanoyl]isoxazolidine-3-carboxamide ¹H NMR (500 MHz, CDCl₃): δ 8.97 (s, 1H), 7.59 (d, 1H), 7.44-7.50 (m, 2H), 7.27 (d, 1H), 4.69 (dd, 1H), 4.63 (dd, 1H), 4.27 (d, 2H), 4.18 (ddd, 1H), 3.93 (q, 1H), 2.80-2.88 (m, 1H), 2.47-2.55 (m, 1H), 1.40 (d, 2H), 1.01 (s, 9H). HRMS (ESI) calculated for $C_{19}H_{26}ClN_6O_4$ 437.1704 (M+H)⁺. found 437.1700.

Example 47

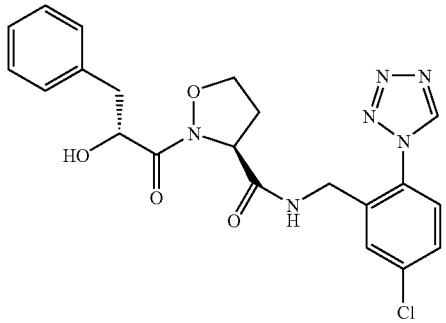

(3S)—N-[5-Chloro-2-(1H-tetrazol-1-yl)benzyl]-2-[(2R)-2-hydroxy-3-phenylpropanoyl]isoxazolidine-3-carboxamide ¹H NMR (500 MHz, CDCl₃): δ 8.97 (s, 1H), 7.59 (d, 1H), 7.48 (dd, 1H), 7.45 (bt, 1H), 7.20-7.35 (m, 6H), 4.85 (ddd, 1H), 4.66 (dd, 1H), 4.24-4.34 (m, 2H), 4.06 (ddd, 1H), 3.40 (q, 1H), 3.23 (d, 1H), 3.02 (dd, 1H), 2.97 (dd, 1H), 2.76-2.84 (m, 1H), 2.32-2.40 (m, 1H). HRMS (ESI) calculated for $C_{21}H_{22}ClN_6O_4$ 457.1391 (M+H)⁺. found 457.1394.

Example 48

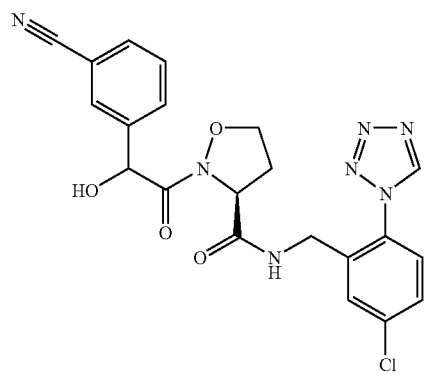

(3S)—N-[5-Chloro-2-(1H-tetrazol-1-yl)benzyl]-2-[(3-cyanophenyl)(hydroxy)acetyl]isoxazolidine-3-carboxamide ¹H NMR (400 MHz, CDCl₃) for the most potent isomer: δ 8.95 (s, 1H), 7.60-7.70 (m, 4H), 7.45-7.52 (m, 2H), 7.25-7.31 (m, 2H), 5.54 (s, 1H), 4.63 (dd, 1H), 4.31 (d, 2H), 3.97 (ddd, 1H), 2.98 (ddd, 1H), 2.70 (dddd, 1H), 2.34 (dddd, 1H). HRMS (ESI) calculated for $C_{21}H_{19}ClN_7O_4$ 468.1187 (M+H)⁺. found 468.1223.

Example 49

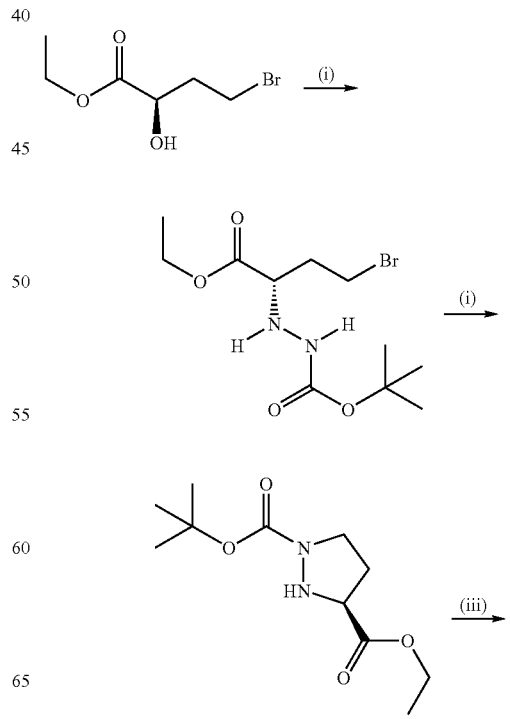

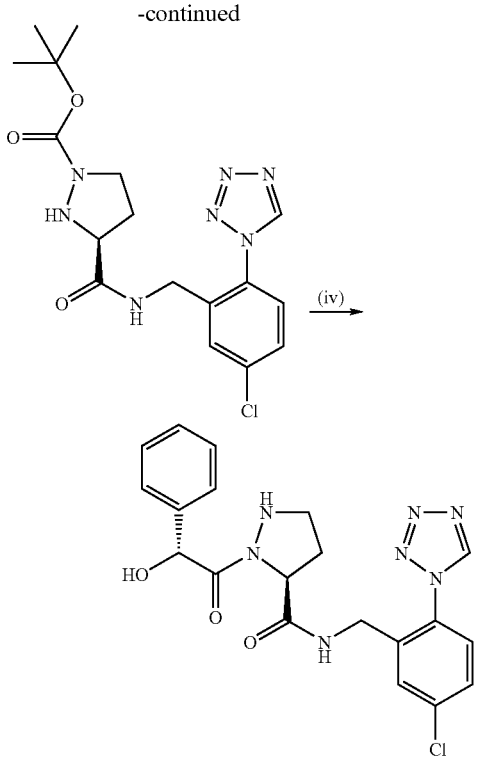

(3S)—N-[5-Chloro-2-(1H-tetrazol-1-yl)benzyl]-2-
[(2R)-2-hydroxy-2-phenylacetyl]pyrazolidine-3-
carboxamide (i) tert-Butyl 2-[(1S)-3-bromo-1-(ethoxycarbonyl)
propyl]hydrazinecarboxylate To a solution of ethyl (2R)-4-bromo-2-hydroxybutanoate (1.1 g, 5.2 mmol, prepared as described in *J. Med. Chem.* 2003, 46, 2057 or *J. Am. Chem. Soc.*, 2004, 126, 12432 and *Tetrahedron Letters* 1997, 38, 4935-4938, in dry DCM (20 mL) at 0° C. was added Tf$_2$O (1.62 g, 5.7 mmol) via syringe. After 5 min, 2,6-lutidine (0.67 g, 6.2 mmol) was added. After another 5 min, t-butylcarbazate (1.38 g, 10.4 mmol) in DCM (5 mL) was added. The solution was allowed to attain rt and stirred overnight. The solvent was evaporated and the residue was purified using flash chromatography (heptane/EtOAc 4:1, 3:1, 2:1) to give the slightly impure tert-butyl 2-[(1S)-3-bromo-1-(ethoxycarbonyl)propyl]hydrazinecarboxylate (1.65 g, 97%) as an oil.

(ii) 1-tert-Butyl 3-ethyl
(3S)-pyrazolidine-1,3-dicarboxylate

To a solution of slightly impure tert-butyl 2-[(1S)-3-bromo-1-(ethoxycarbonyl)propyl]hydrazinecarboxylate (1.57 g, 4.83 mmol) in dry THF (50 mL) at 0° C. was added LiHMDS (1 M in THF, 4.83 mmol, 4.83 mL). The solution was allowed to attain rt and was then stirred for 2 h. The reaction was quenched by addition of saturated NH$_4$Cl(aq) and diluted with TBME. The phases were separated, the organic phase was dried, filtered and evaporated. The residue was purified using flash chromatography (DCM/EtOAc 4:1, 1:1) to give the pure 1-tert-butyl 3-ethyl (3S)-pyrazolidine-1,3-dicarboxylate (610 mg, 52%) as an oil.

1HNMR (CDCl$_3$) 500 MHz: δ 1.30 (t, 3H), 1.51 (s, 9H), 2.13 (m, 1H), 2.41 (m, 1H), 3.48 (m, 1H), 3.65 (m, 1H), 3.88 (t, 1H), 4.24 (m, 2H), 4.55 (bs, 1H).

(iii) tert-Butyl (3S)-3-{[5-chloro-2-(1H-tetrazol-1-yl)
benzyl]carbamoyl}pyrazolidine-1-carboxylate To a solution of (S)-pyrazolidine-1,3-dicarboxylic acid 1-tert-butyl ester 3-ethyl ester
(1.920 g, 7.86 mmol) in THF (60 mL) was added a solution of lithium hydroxide (188 mg, 7.86 mmol in 20 mL water) and the mixture was stirred at rt for 1 h. The solvents were evaporated and the solid residue was suspended in DCM (70 mL). To this suspension was added 5-chloro-2-tetrazol-1-yl-benzylamine hydrochloride (2.13 g, 8.645 mmol, prepared as described in *J. Med. Chem.* 2004, 47, 2995), hydroxybenzotriazole (1.17 g, 8.645 mmol, as a solution in 10 mL DMF), followed by EDC (2.26 g, 11.79 mmol) and triethylamine (0.795 mg, 7.895 mmol). The resulting mixture was stirred at rt for 3 h and was then diluted with EtOAc and washed with 1 M HCl, saturated NaHCO$_3$(aq) and brine. The organic phase was dried, filtered, evaporated and purified using flash chromatography (EtOAc, then EtOAc/MeOH gradient from 20:1 to 10:1) to give tert-butyl (3S)-3-{[5-chloro-2-(1H-tetrazol-1-yl)benzyl]carbamoyl}pyrazolidine-1-carboxylate (2.05 g, 64%) as an oil.

(iv) (3S)—N-[5-Chloro-2-(1H-tetrazol-1-yl)benzyl]-
2-[(2R)-2-hydroxy-2-phenylacetyl]pyrazolidine-3-
carboxamide To a solution of tert-butyl (3S)-3-{[5-chloro-2-(1H-tetrazol-1-yl)benzyl]carbamoyl}pyrazolidine-1-carboxylate (82 mg, 0.200 mmol) in DCM (2 mL) and pyridine (0.080 mL) was added a solution of (R)-2-phenyl-2-(trimethylsilyloxy) acetyl chloride (ca 0.3 M in DCM, 1 mL, 0.3 mmol, see Preparation 2). The resulting solution was stirred at rt overnight. TFA (ca 1 mL) was added and the mixture was stirred for one more hour and then evaporated. The residue was purified using flash chromatography (DCM/MeCN gradient from 2:1 to 1:1) to give (3S)—N-[5-chloro-2-(1H-tetrazol-1-yl)benzyl]-2-[(2R)-2-hydroxy-2-phenylacetyl]pyrazolidine-3-carboxamide (52 mg, 59%) as an oil.

$^1$H NMR (500 MHz, CDCl$_3$): δ 9.04 (s, 1H), 7.69 (bt, 1H), 7.61 (d, 1H), 7.45 (dd, 1H), 7.35-7.38 (m, 2H), 7.25-7.33 (m, 4H), 5.61 (d, 1H), 4.51 (d, 1H), 4.42 (t, 1H), 4.35 (dd, 1H), 4.18-4.26 (m, 2H), 3.01-3.08 (m, 1H), 2.25-2.35 (m, 1H), 2.14-2.17 (m, 2H). HRMS (ESI) calculated for C$_{20}$H$_{21}$ClN$_7$O$_3$ 442.1394 (M+H)$^+$. found 442.1418.

Examples 50-57 were prepared in a manner analogous to Example 49 described above using the appropriate starting materials.

Example 50

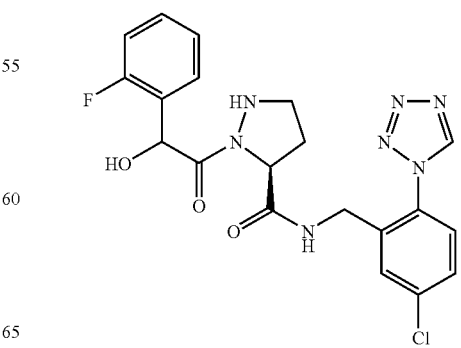

(3S)—N-[5-Chloro-2-(1H-tetrazol-1-yl)benzyl]-2-[(2-fluorophenyl)(hydroxy)acetyl]pyrazolidine-3-carboxamide ¹H NMR (500 MHz, CDCl₃) for the most potent isomer: δ 9.04 (s, 1H), 7.65-7.58 (m, 2H), 7.45 (dd, 1H), 7.30-7.18 (m, 3H), 7.07 (t, 1H), 7.01 (dd, 1H), 5.78 (s, 1H), 4.47 (dd, 1H), 4.36 (dd, 1H), 4.22 (dd, 1H), 4.14 (br. d, 1H), 2.96 (br. dd, 1H), 2.31 (m, 1H), 2.13 (m, 1H), 1.96-1.81 (m, 1H). HRMS (ESI) calculated for C₂₀H₂₀ClFN₇O₃ 460.1300 (M+H)⁺. found 460.1314.

Example 51

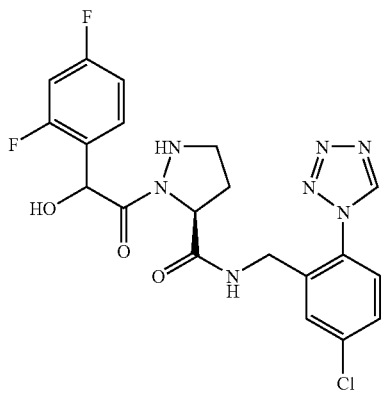

(3S)—N-[5-Chloro-2-(1H-tetrazol-1-yl)benzyl]-2-[(2,4-difluorophenyl)(hydroxy)acetyl]pyrazolidine-3-carboxamide ¹H NMR (500 MHz, CDCl₃) for the most potent isomer: δ 9.03 (s, 1H), 7.62 (d, 1H), 7.55 (bt, 1H), 7.48 (dd, 1H), 7.30 (d, 1H), 7.22 (ddd, 1H), 6.76-6.86 (m, 2H), 5.75 (s, 1H), 4.48 (t, 1H), 4.39 (dd, 1H), 4.30 (bs, 1H), 4.23 (dd, 1H), 4.16 (dd, 1H), 3.02 (ddd, 1H), 2.32-2.40 (m, 1H), 2.13-2.20 (m, 1H), 1.87-1.97 (m, 1H). HRMS (ESI) calculated for C₂₀H₁₉ClF₂N₇O₃ 478.1206 (M+H)⁺. found 478.1201.

Example 52

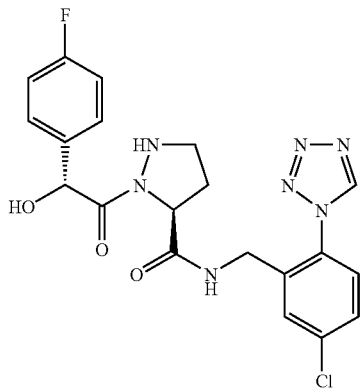

(3S)—N-[5-Chloro-2-(1H-tetrazol-1-yl)benzyl]-2-[(2R)-2-(4-fluorophenyl)-2-hydroxyacetyl]pyrazolidine-3-carboxamide ¹H NMR (500 MHz, CDCl₃) for the most potent isomer: δ 9.00 (s, 1H), 7.62 (d, 1H), 7.55 (bt, 1H), 7.48 (dd, 1H), 7.35-7.40 (m, 2H), 7.30 (d, 1H), 6.96-7.03 (m, 2H), 5.62 (d, 1H), 4.37-4.45 (m, 2H), 4.21 (dd, 1H), 3.08 (dd, 1H), 2.30-2.44 (m, 1H), 2.05-2.20 (m, 2H). HRMS (ESI) calculated for C₂₀H₂₀ClFN₇O₃ 460.1300 (M+H)⁺. found 460.1302.

Example 53

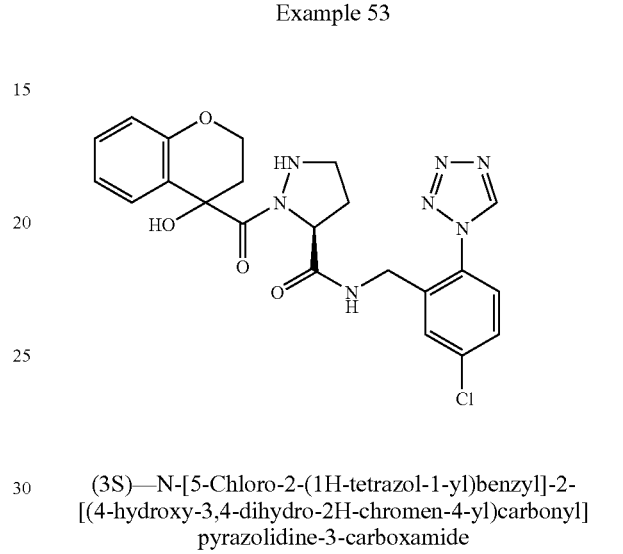

(3S)—N-[5-Chloro-2-(1H-tetrazol-1-yl)benzyl]-2-[(4-hydroxy-3,4-dihydro-2H-chromen-4-yl)carbonyl]pyrazolidine-3-carboxamide ¹H NMR (500 MHz, CDCl₃) for the most potent isomer: δ 9.05 (s, 1H), 7.69 (d, 1H), 7.45-7.55 (m, 2H), 7.30 (d, 1H), 7.10-7.17 (m, 1H), 6.67-6.85 (m, 3H), 5.12 (bs, 1H), 4.56 (dd, 1H), 4.15-4.45 (m, 4H), 3.35-3.42 (m, 1H), 3.12-3.22 (m, 1H), 2.60-2.80 (m, 2H), 2.20-2.40 (m, 2H), 1.94 (dt, 1H). HRMS (ESI) calculated for C₂₂H₂₃ClN₇O₄ 484.1500 (M+H)⁺. found 484.1503.

Example 54

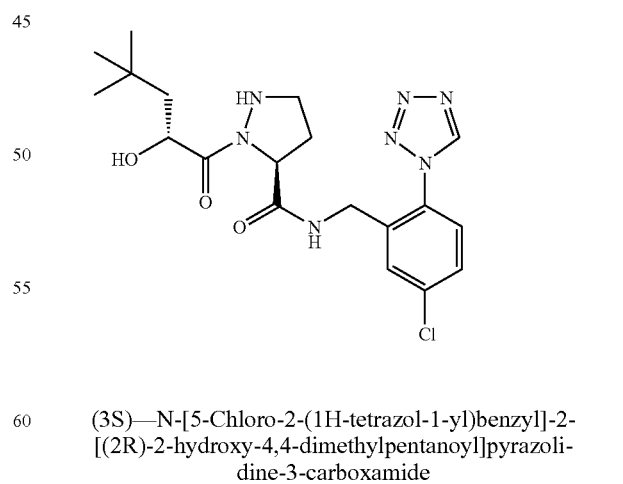

(3S)—N-[5-Chloro-2-(1H-tetrazol-1-yl)benzyl]-2-[(2R)-2-hydroxy-4,4-dimethylpentanoyl]pyrazolidine-3-carboxamide ¹H NMR (500 MHz, CDCl₃): δ 9.02 (s, 1H), 7.64 (bt, 1H), 7.59 (d, 1H), 7.46 (dd, 1H), 7.28 (d, 1H), 4.69 (dd, 1H), 4.52 (t, 1H), 4.40 (dd, 1H), 4.18 (dd, 1H), 3.33 (dd, 1H), 2.75 (ddd, 1H), 2.46-2.56 (m, 1H), 2.27-2.37 (m, 1H), 1.46 (dd, 1H), 1.35 (dd, 1H), 1.01 (s, 9H). HRMS (ESI) calculated for $C_{19}H_{27}ClN_7O_3$ 436.1864 (M+H)$^+$. found 436.1881.

Example 55

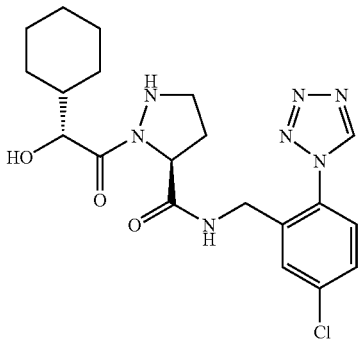

(3S)—N-[5-Chloro-2-(1H-tetrazol-1-yl)benzyl]-2-[(2R)-2-cyclohexyl-2-hydroxyacetyl]pyrazolidine-3-carboxamide $^1$H NMR (500 MHz, CD$_3$OD): δ 9.54 (s, 1H), 7.72 (d, 1H), 7.55 (dd, 1H), 7.48 (d, 1H), 4.38-4.43 (m, 2H), 4.25 (s, 2H), 3.23 (ddd, 1H), 2.73 (ddd, 1H), 2.41-2.48 (m, 1H), 1.95-2.03 (m, 1H), 1.50-1.80 (m, 6H), 1.06-1.32 (m, 5H). HRMS (ESI) calculated for $C_{20}H_{27}ClN_7O_3$ 448.1864 (M+H)$^+$. found 448.1859.

Example 56

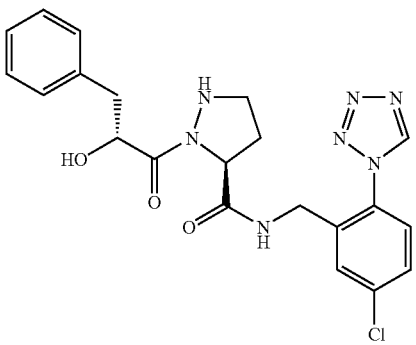

(3S)—N-[5-Chloro-2-(1H-tetrazol-1-yl)benzyl]-2-[(2R)-2-hydroxy-3-phenylpropanoyl]pyrazolidine-3-carboxamide $^1$H NMR (500 MHz, CD$_3$OD): δ 9.53 (s, 1H), 7.70 (d, 1H), 7.54 (dd, 1H), 7.47 (d, 1H), 7.05-7.28 (m, 5H), 4.93 (dd, 1H), 4.35 (t, 1H), 4.24 (s, 2H), 3.10-3.17 (m, 1H), 3.01 (dd, 1H), 2.79 (dd, 1H), 2.32-2.46 (m, 2H), 1.90-2.00 (m, 1H). HRMS (ESI) calculated for $C_{21}H_{23}ClN_7O_3$ 456.1551 (M+H)$^+$. found 456.1531.

Example 57

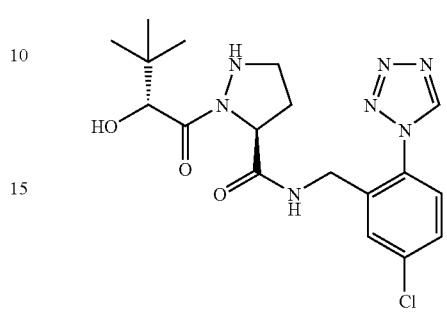

(3S)—N-[5-Chloro-2-(1H-tetrazol-1-yl)benzyl]-2-[(2R)-2-hydroxy-3,3-dimethylbutanoyl]pyrazolidine-3-carboxamide $^1$H NMR (500 MHz, CDCl$_3$): δ 9.03 (s, 1H), 7.68 (bt, 1H), 7.59 (d, 1H), 7.47 (dd, 1H), 7.28 (d, 1H), 4.62 (dd, 1H), 4.46 (dd, 1H), 4.37 (d, 1H), 4.28 (dd, 1H), 4.10-4.25 (m, 2H), 3.30-3.37 (m, 1H), 2.78-2.88 (m, 1H), 2.54-2.64 (m, 1H), 2.25-2.33 (m, 1H), 0.97 (s, 9H). HRMS (ESI) calculated for $C_{18}H_{25}ClN_7O_3$ 422.1707 (M+H)$^+$. found 422.1708.

Biological Tests

The following test procedures may be employed:

Test A

Determination of Thrombin Inhibition with a Chromogenic, Robotic Assay

The thrombin inhibitor potency is measured with a chromogenic substrate method, in a Plato 3300 robotic microplate processor (Rosys AG, CH-8634 Hombrechtikon, Switzerland), using 96-well, half volume microtitre plates (Costar, Cambridge, Mass., USA; Cat No 3690). Stock solutions of test substance in DMSO (72 μL), 0.1-1 mmol/L, are diluted serially 1:3 (24+48 μL) with DMSO to obtain ten different concentrations, which are analyzed as samples in the assay. 2 μL of test sample is diluted with 124 μL assay buffer, 12 μL of chromogenic substrate solution (S-2366, Chromogenix, Mölndal, Sweden) in assay buffer and finally 12 μL of α-thrombin solution (Human α-thrombin, Sigma Chemical Co. or Hematologic Technologies) in assay buffer, are added, and the samples mixed. The final assay concentrations are: test substance 0.00068-133 μmol/L, S-2366 0.30 mmol/L, α-thrombin 0.020 NIHU/mL. The linear absorbance increment during 40 minutes incubation at 37° C. is used for calculation of percentage inhibition for the test samples, as compared to blanks without inhibitor. The IC$_{50}$ value, corresponding to the inhibitor concentration which causes 50% inhibition of the thrombin activity, is calculated from a log concentration vs. % inhibition curve.

Test B

Determination of Activated Partial Thromboplastin Time (APTT)

APTT is determined in pooled normal human citrated plasma with the reagent PTT Automated 5 manufactured by Stago. The inhibitors are added to the plasma (10 μL inhibitor solution to 90 μL plasma) and incubated with the APTT reagent for 3 minutes followed by the addition of 100 μL of calcium chloride solution (0.025 M) and APTT is determined by use of the coagulation analyzer KC10 (Amelung) according to the instructions of the reagent producer.

The clotting time is expressed as absolute values (seconds) as well as the ratio of APTT without inhibitor ($APTT_0$) to APTT with inhibitor ($APTT_i$). The latter ratios (range 1-0) are plotted against the concentration of inhibitor (log transformed) and fitted to sigmoidal dose-response curves according to the equation $$y=a/[1+(x/IC_{50})^s]$$

where: a=maximum range, i.e. 1; s=slope of the dose-response curve; and $IC_{50}$=the concentration of inhibitor that doubles the clotting time. The calculations are processed on a PC using the software program GraFit Version 3, setting equation equal to: Start at 0, define end=1 (Erithacus Software, Robin Leatherbarrow, Imperial College of Science, London, UK).

$IC_{50}$APTT is defined as the concentration of inhibitor in human plasma that doubled the Activated Partial Thromboplastin Time.

RESULTS

Compounds of the Examples were tested in Test A as described above and were found to exhibit $IC_{50}$ values of less than 1 µM. The following table shows the $IC_{50}$ values for a representative selection of compounds:

| Example No. | Test A $IC_{50}$ (nM) |
|---|---|
| 1 | 4 |
| 2 | 34 |
| 3 | 22 |
| 4 | 18 |
| 5 | 24 |
| 6 | 35 |
| 7 | 5.7 |
| 8 | 5.8 |
| 9 | 32 |
| 10 | 11 |
| 11 | 21 |
| 12 | 130 |
| 13 | 7.8 |
| 14 | 8.5 |
| 15 | 6.3 |
| 16 | 44 |
| 17 | 20 |
| 18 | 3.5 |
| 19 | 31 |
| 20 | 28 |
| 21 | 25 |
| 22 | 740 |
| 23 | 193 |
| 24 | 140 |
| 25 | 160 |
| 26 | 150 |
| 27 | 140 |
| 28 | 120 |
| 29 | 13 |
| 30 | 660 |
| 31 | 9.7 |
| 32 | 170 |
| 33 | 100 |
| 34 | 160 |
| 35 | 70 |
| 36 | 94 |
| 37 | 16 |
| 38 | 43 |
| 39 | 13 |
| 40 | 44 |
| 41 | 41 |
| 42 | 21 |
| 43 | 68 |
| 44 | 26 |
| 45 | 32 |
| 46 | 40 |
| 47 | 80 |
| 48 | 92 |
| 49 | 16 |
| 50 | 79 |
| 51 | 63 |
| 52 | 8.4 |
| 53 | 240 |
| 54 | 24 |
| 55 | 8.4 |
| 56 | 79 |
| 57 | 27 |

The invention claimed is:

1. A compound which is (5S)—N-[5-chloro-2-(1H-tetrazol-1-yl)benzyl]-1-[(2R)-2-(4-fluorophenyl)-2-hydroxyacetyl]-4,5-dihydro-1H-pyrazole-5-carboxamide

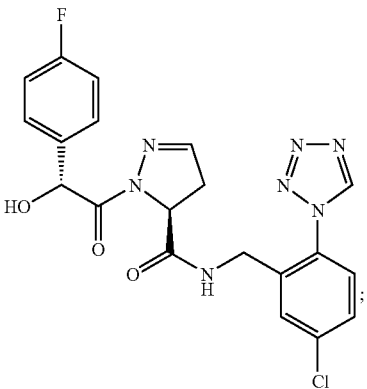

or a pharmaceutically acceptable salt of said compound.

2. A pharmaceutical formulation comprising a compound, or pharmaceutically acceptable salt thereof, according to claim 1 in admixture with at least one pharmaceutically acceptable carrier, excipient or diluent.

3. A compound which is (1R)-2-[(5S)-5-{[5-chloro-2-(1H-tetrazol-1-yl)benzyl]carbamoyl}-4,5-dihydro-1H-pyrazol-1-yl]-1-(4-fluorophenyl)-2-oxoethyl propanoate

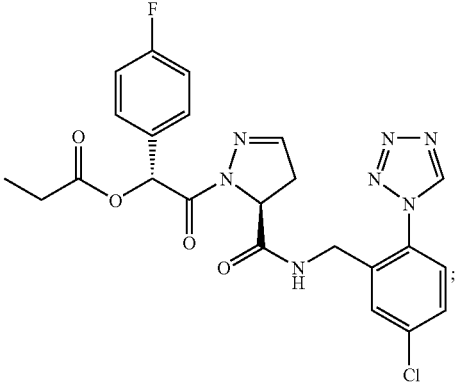

or a pharmaceutically acceptable salt of said compound.

4. A pharmaceutical formulation comprising a compound, or pharmaceutically acceptable salt thereof, according to claim 3 in admixture with at least one pharmaceutically acceptable carrier, excipient or diluent.

* * * * *